(12) United States Patent
Shepherd

(10) Patent No.: US 11,773,423 B2
(45) Date of Patent: Oct. 3, 2023

(54) PRODUCTION OF ACTIVATED TDP-DEOXYSUGARS IN RECOMBINANT MICROORGANISMS

(71) Applicant: ZuChem, Inc., Chicago, IL (US)

(72) Inventor: Micah Douglas Shepherd, Melrose, MA (US)

(*) Notice: Subject to any disclaimer, the term of this patent is extended or adjusted under 35 U.S.C. 154(b) by 0 days.

(21) Appl. No.: 15/753,378

(22) PCT Filed: Aug. 17, 2016

(86) PCT No.: PCT/US2016/047315
§ 371 (c)(1),
(2) Date: Feb. 19, 2018

(87) PCT Pub. No.: WO2017/031189
PCT Pub. Date: Feb. 23, 2017

(65) Prior Publication Data
US 2018/0245118 A1 Aug. 30, 2018

Related U.S. Application Data

(60) Provisional application No. 62/205,893, filed on Aug. 17, 2015.

(51) Int. Cl.
| | | |
|---|---|---|
| *C12P 19/60* | (2006.01) | |
| *C12P 19/18* | (2006.01) | |
| *C12N 9/12* | (2006.01) | |
| *C12N 9/88* | (2006.01) | |
| *A61K 35/66* | (2015.01) | |
| *C12N 9/90* | (2006.01) | |
| *C12N 9/10* | (2006.01) | |
| *C12N 9/04* | (2006.01) | |
| *A61K 35/00* | (2006.01) | |

(52) U.S. Cl.
CPC .............. *C12P 19/60* (2013.01); *A61K 35/66* (2013.01); *C12N 9/0006* (2013.01); *C12N 9/1029* (2013.01); *C12N 9/1096* (2013.01); *C12N 9/1241* (2013.01); *C12N 9/88* (2013.01); *C12N 9/90* (2013.01); *C12P 19/18* (2013.01); *C12Y 101/01049* (2013.01); *C12Y 206/01* (2013.01); *C12Y 207/07024* (2013.01); *C12Y 402/01046* (2013.01); *C12Y 501/03013* (2013.01); *A61K 35/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,431,139 B2* | 4/2013 | Telford ................ | C07K 14/315 424/244.1 |
| 9,796,764 B2* | 10/2017 | Poth ..................... | C07K 14/415 |
| 2012/0041185 A1 | 2/2012 | Wang et al. | |
| 2014/0024082 A1 | 1/2014 | Woodyer et al. | |

OTHER PUBLICATIONS

Amann et al., "(Chemo) Enzymatic Synthesis of dTDP-Activated 2, 6-Dideoxysugars as Building Blocks of Polyketide Antibiotics," Carbohydrate Research, 335:23-32 (2001).
Arabshahi et al., "Galactose-1-phosphate Uridylyltransferase. Purification of the Enzyme and Stereochemical Course of Each Step of the Double-Displacement Mechanism," Biochemistry, 25:5583-5589 (1986).
Ballicora et al., "ADP-Glucose Pyrophosphorylase, a Regulatory Enzyme for Bacterial Glycogen Synthesis," Microbiology and Molecular Biology Reviews, 67(2): 213-225 (2003).
Borisova et al., "Characterization of the Glycosyltransferase Activity of DesVII: Analysis of and Implications for the Biosynthesis of Macrolide Antibiotics," J. American Chemical Society, 126:6534-6535 (2004).
Buckstein et al., "Characterization of Nucleotide Pools as a Function of Physiological State in *Escherichia coli*," Journal of Bacteriology, 190(2):718-726 (2008).
Burgard et al., "OptKnock: A Bilevel Programming Framework for Identifying Gene Knockout Strategies for Microbial Strain Optimization," Biotechnology and Bioengineering, 85(7):2-11 (2003).
Chen et al., "Functional Characterization and Substrate Specificity of Spinosyn Rhamnosyltransferase by in Vitro Reconstitution of Spinosyn Biosynthetic Enzymes," The Journal of Biological Chemistry 284(11):7352-7363 (2009).
Gon et al., "Increase in dNTP pool size during the DNA damage response plays a key role in spontaneous and induced-mutagenesis in *Escherichia coli*," PNAS 108(48):19311-19316 (2011).
Huang et al., "Capsule deletion via a λ-Red knockout system perturbs biofilm formation and fimbriae expression in Klebsiella pneumoniae MGH 78578," BMC Research Notes, 7:1-8 (2014).
International Search Report dated Nov. 3, 2016 in connection with International Application No. PCT/US/2016/047315, filed on Aug. 17, 2016, 3 pages.
Jiang et al., "Characterization of UDP-Glucose Dehydrogenase and UDP-Glucose Pyrophosphorylase Mutants of Proteus mirabilis: Defectiveness in Polymyxin B Resistance, Swarming and Virulence," Antimicrobial Agents and Chemotherapy, 54(5):2000-2009 (2010).
Kamogawa et al., "Purification and Properties of Uridinediphosphate Glucose Pyrophosphorylase from *Escherichia coli* K 12," The Journal of Biochemistry, 1965; 57(6):758-765.
Leimkuhler et al., "Characterization of rhodosaminyl-transfer by the AknS/AknT glycosylation complex and its use in reconstituting the biosynthetic pathway of Aclacinomycin A," J Am Chem Soc. Aug. 29, 2007; 129(34):10546-10550.
Losey et al., "Tandem Action of Glycosyltransferases in the Maturation of Vancomycin and Teicoplanin Aglycones Novel Glycopeptides," Biochemistry 2001, 40, 4745-4755.

(Continued)

*Primary Examiner* — Hope A Robinson
(74) *Attorney, Agent, or Firm* — McDonnell Boehnen Hulbert & Berghoff LLP

(57) ABSTRACT

The invention provides compositions and methods for the production of TDP-deoxysugars.

6 Claims, 11 Drawing Sheets

(56) References Cited

OTHER PUBLICATIONS

Ma et al., "Formation of dTDP-Rhamnose is Essential for Growth of Mycobacteria," Journal of Bacteriology, 184 (12):3392-3395 (2002).

Peiru et al., "Metabolically engineered *Escherichia coli* for efficient production of glycosylated natural products," Microbial Biotechnolgy, 1(6):476-486 (2008).

Perrier et al., "Genetically Engineered Zinc-chelating Adenylate Kinase from *Escherichia coli* with Enhanced Thermal Stability," Journal of Biological Chemistry, 273:19097-19101 (1998).

Tanizawa, et al., "High Level Expression of Chicken Muscle Adenylate Kinase in *Escherichia coli*," J. Biochem. 101, 1289-1296 (1987).

Wang, et al., "Cooperation of Two Bifunctional Enzymes in the Biosynthesis and Attachment of Deoxysugars of the Antitumor Antibiotic Mithramycin," Angew Chern Int Ed Engl. Oct. 15, 2012; 51(42).

Yuan, et al., "In Vitro Reconstitution of EryCIII Activity for the Preparation of Unnatural Macrolides," J Am Chem Soc. Oct. 19, 2005; 127(41): 14128-14129.

\* cited by examiner

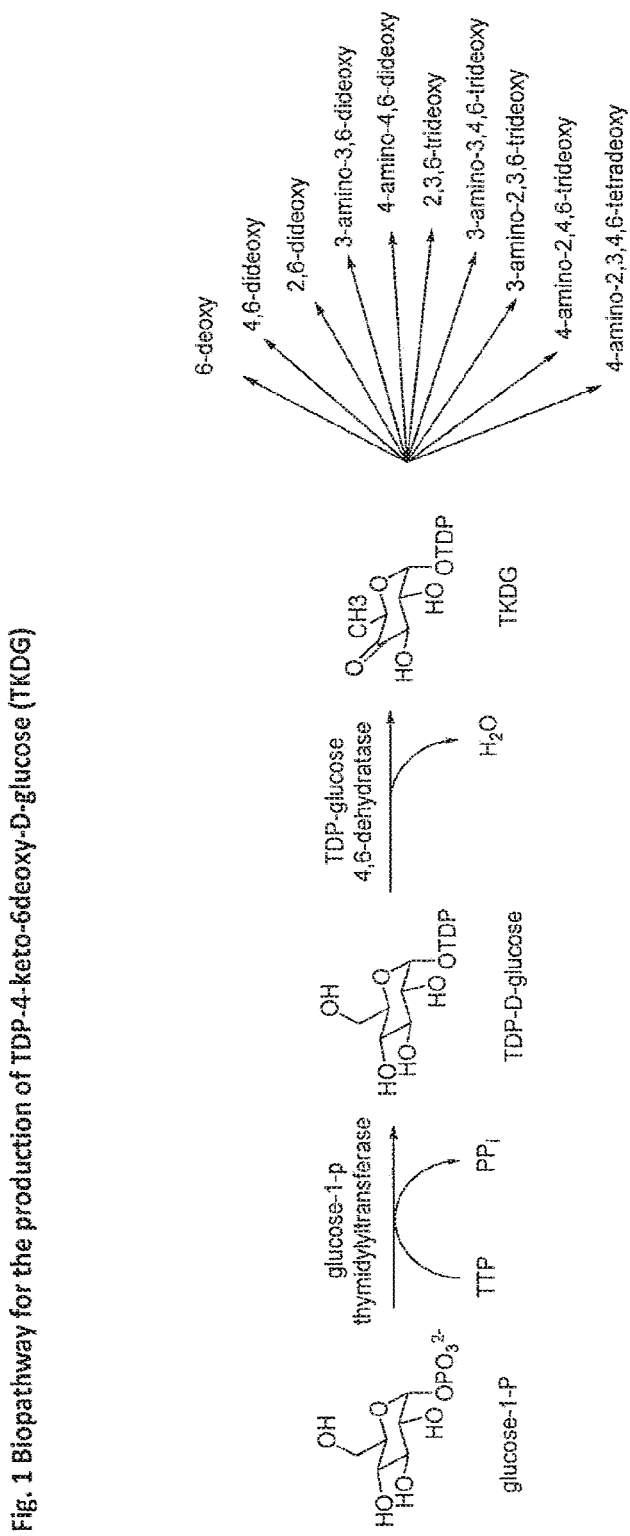
Fig. 1 Biopathway for the production of TDP-4-keto-6deoxy-D-glucose (TKDG)

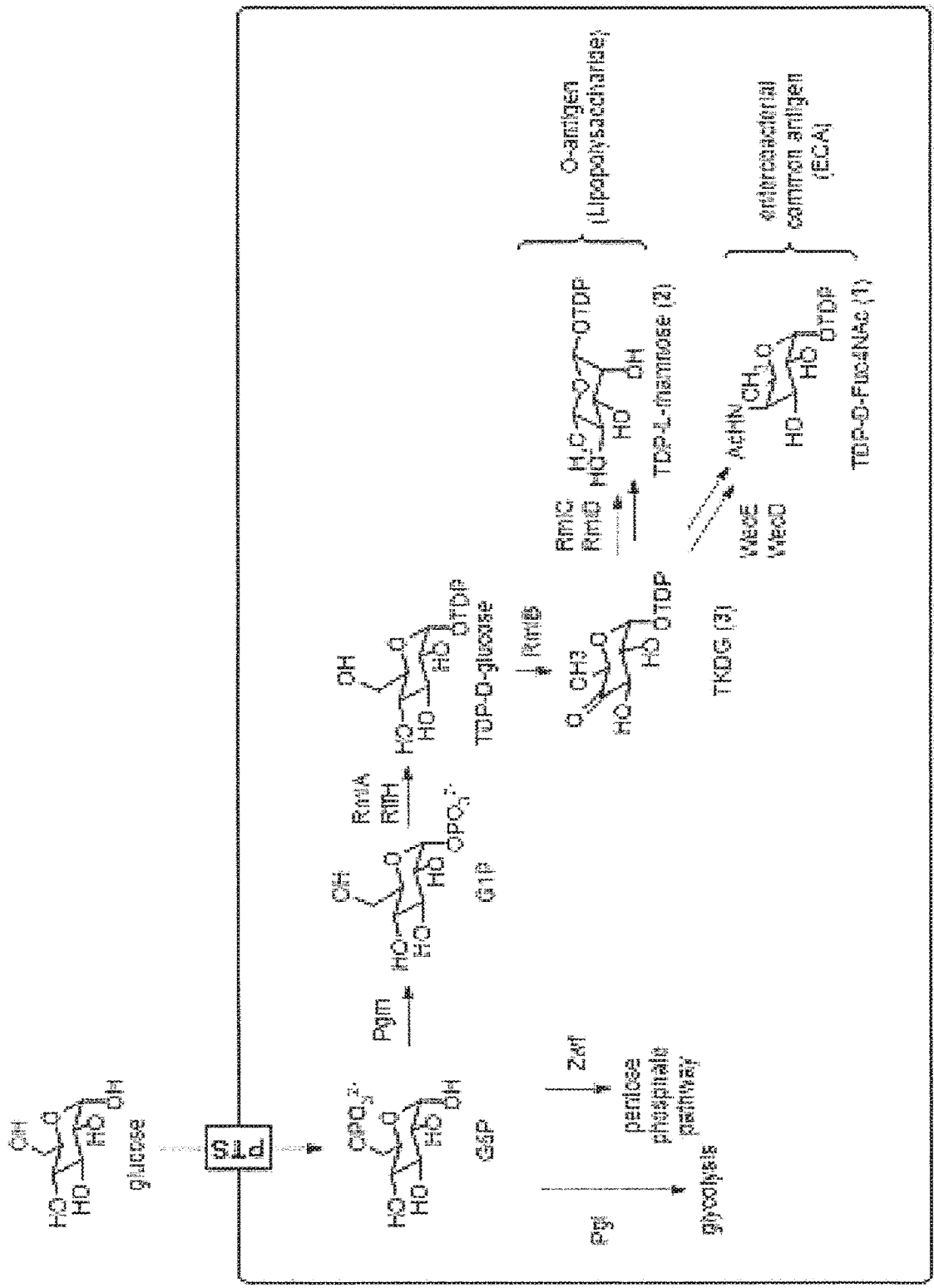

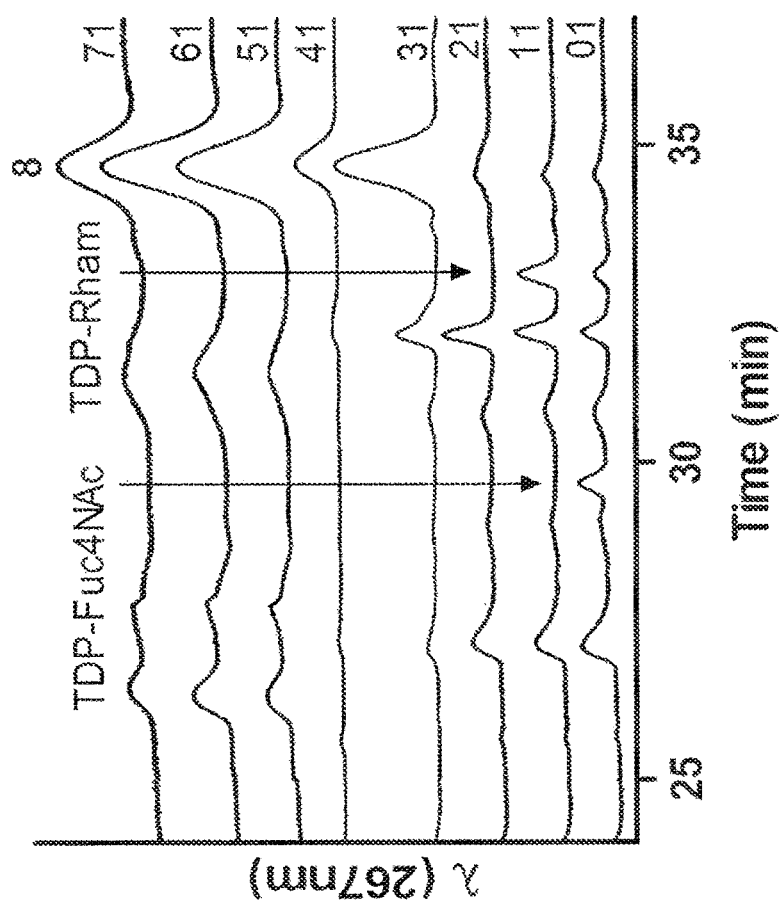
Fig. 3 HPLC traces of zucM01-zucM71 showing TKDG accumulation. Traces are labeled 01-71, respectively.

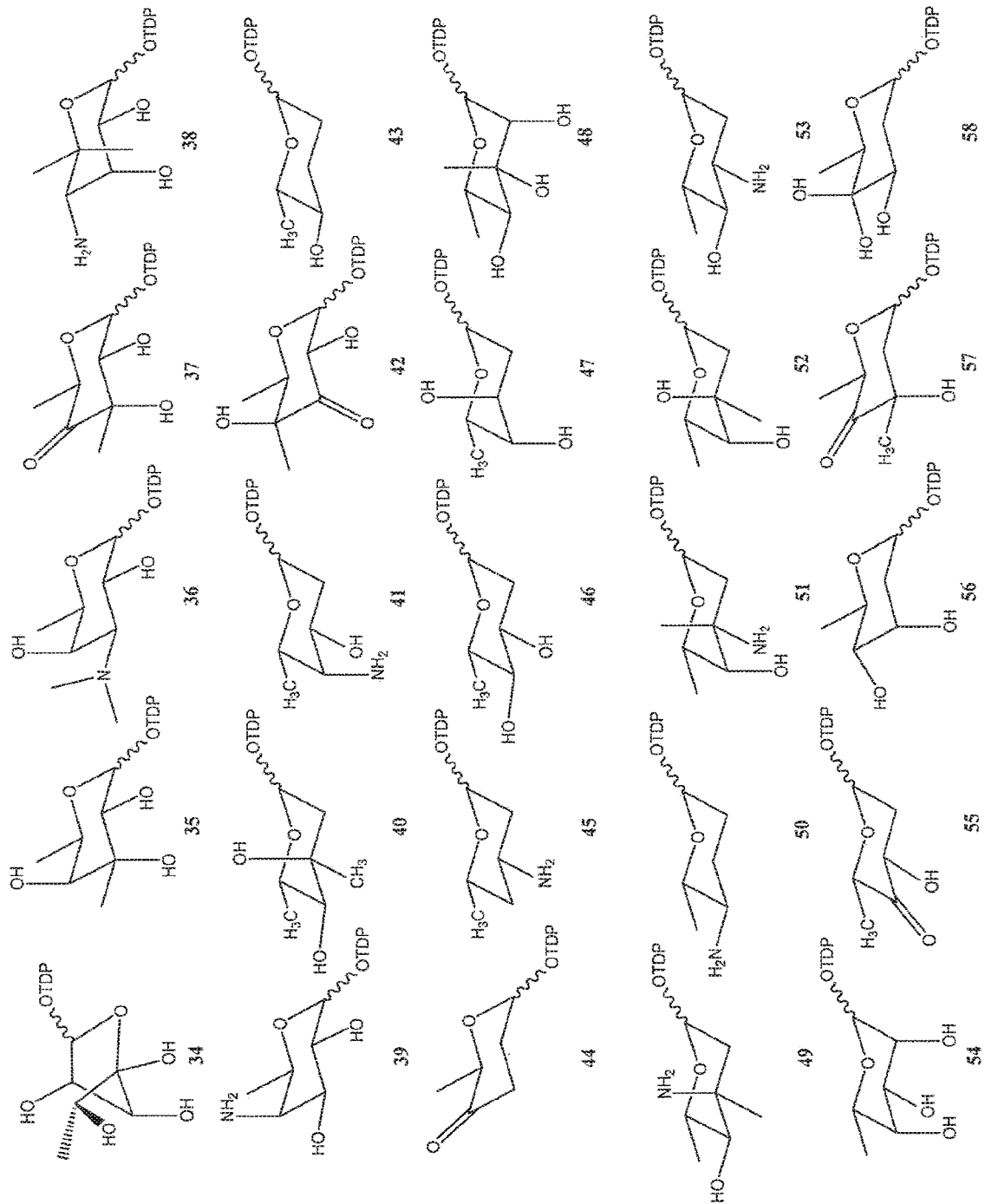
Figure. 4 TDP-deoxysugars utilized in nature. Can be found as α and/or β linked TDP-deoxysugars.

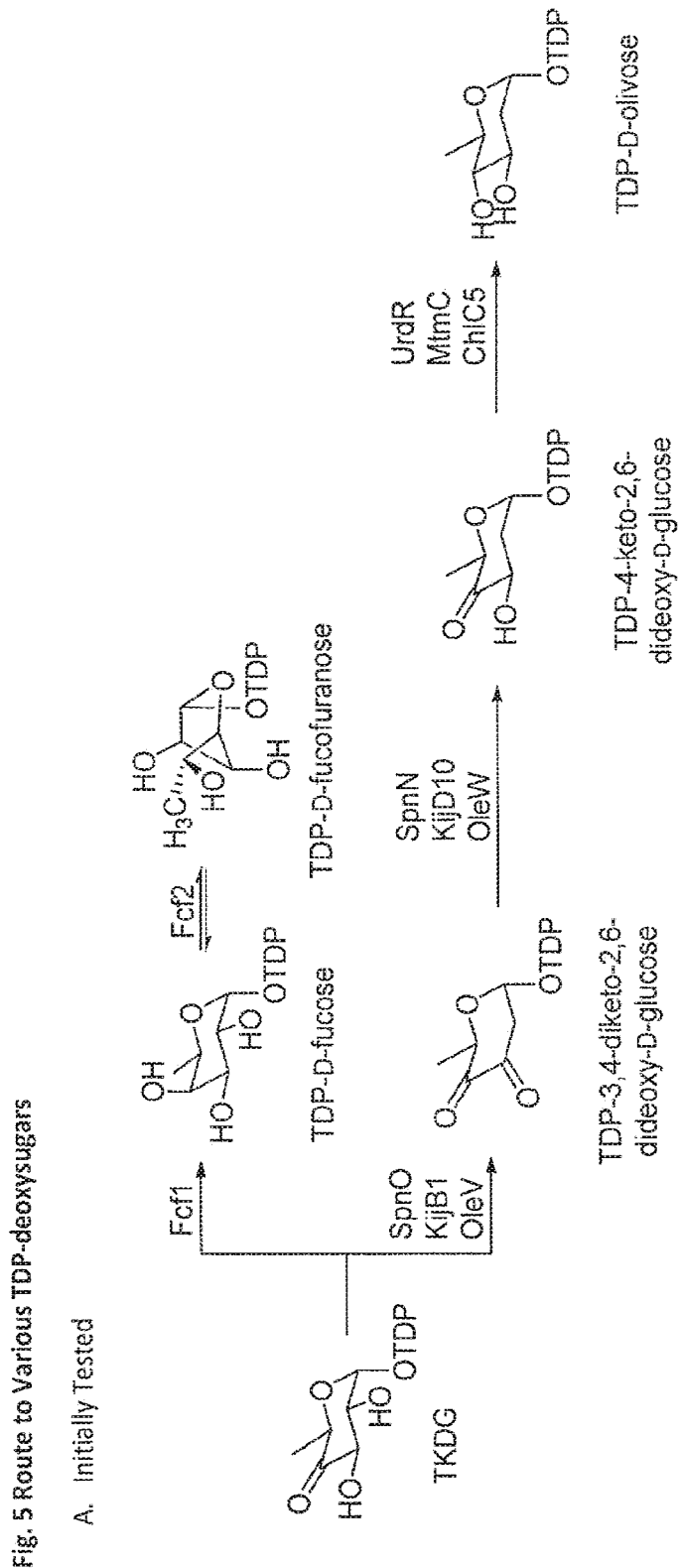

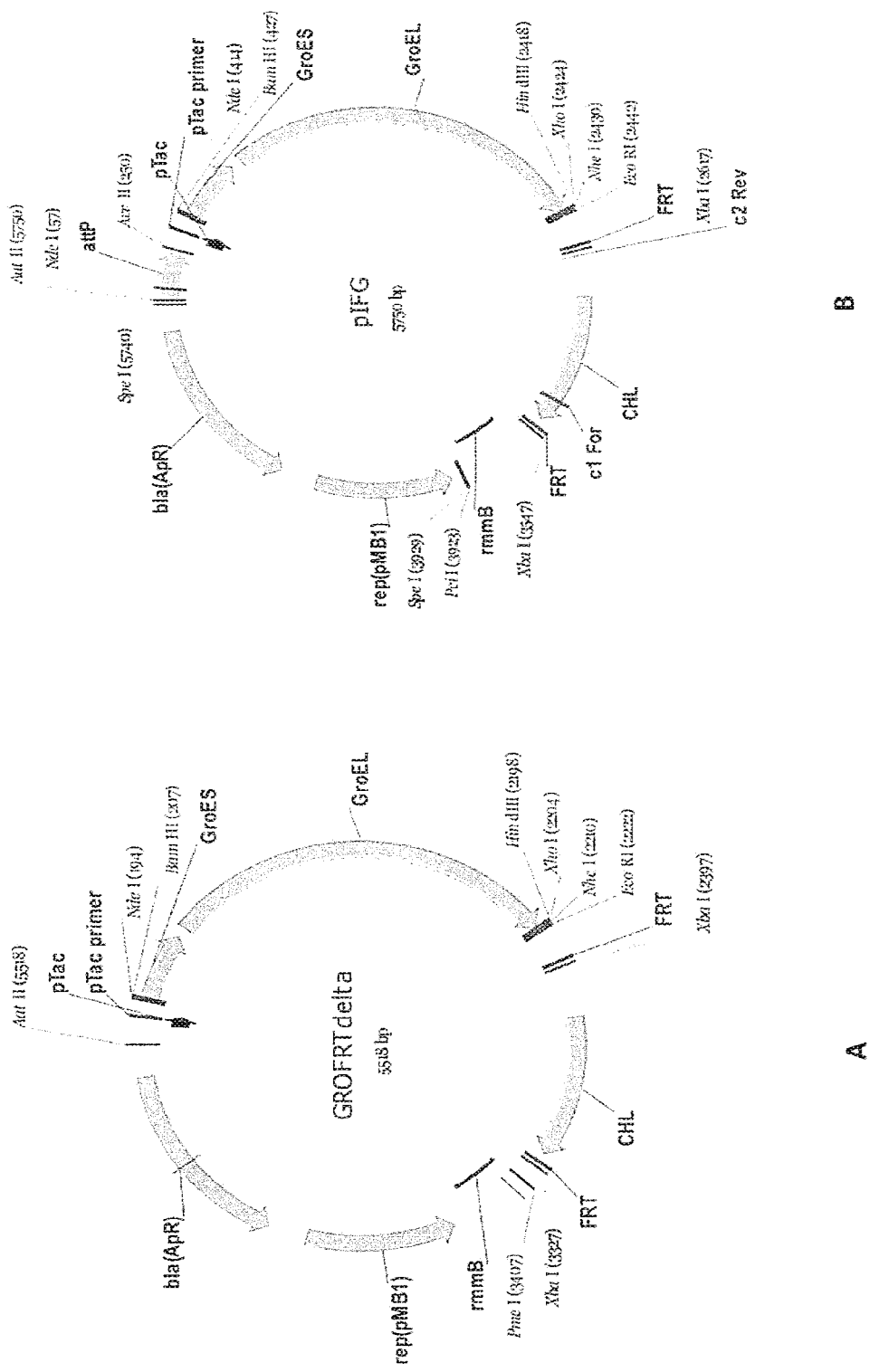
Fig. 6. Plasmids for integration of pathways into genome

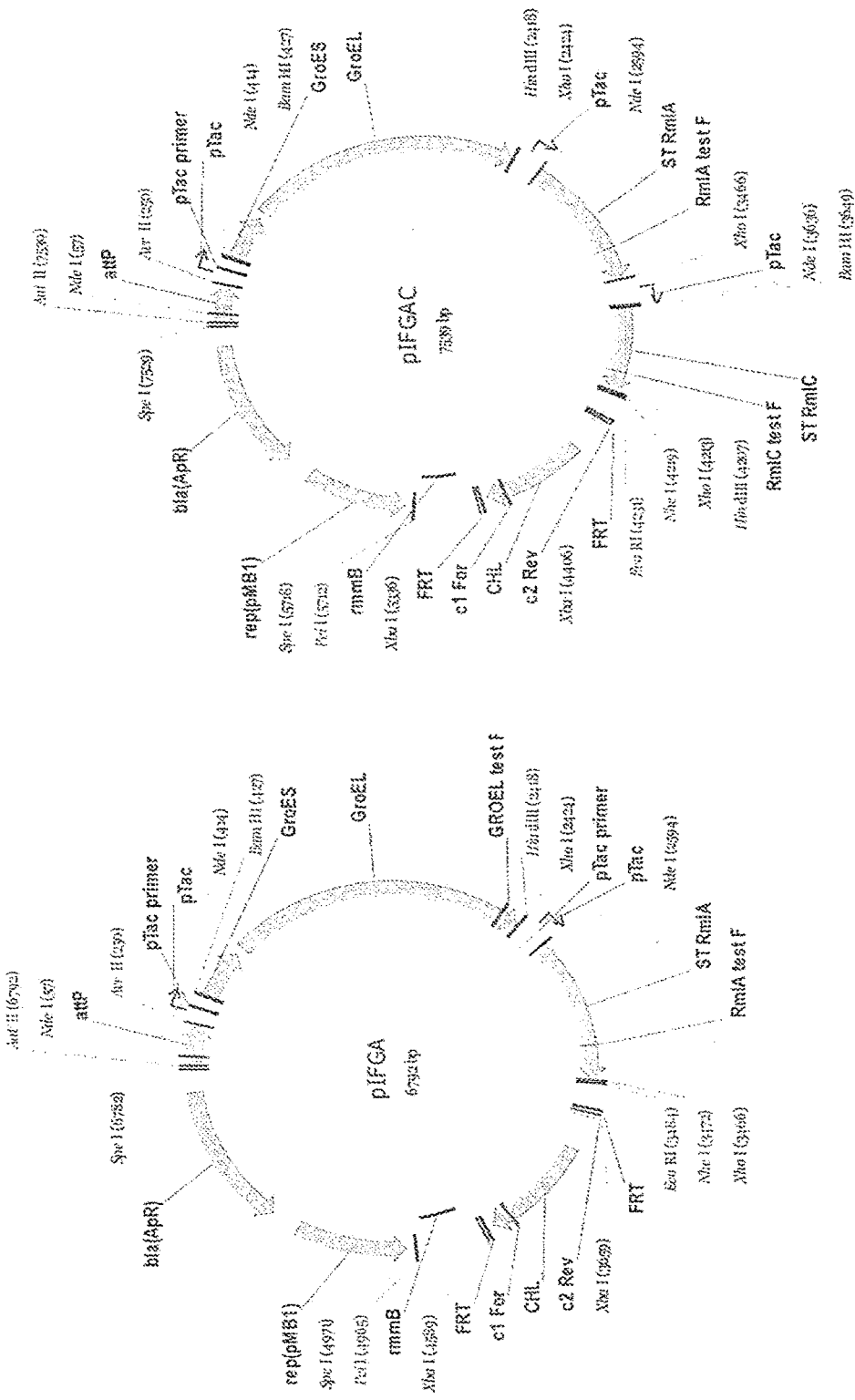
Fig. 7 Additional Integration Vectors

PRODUCTION OF ACTIVATED TDP-DEOXYSUGARS IN RECOMBINANT MICROORGANISMS

PRIORITY

This application is a U.S. National Phase Application pursuant to 35 U.S.C. §371 of International Application No. PCT/US2016/047315 filed on Aug. 17, 2016, which claims the benefit of U.S. Ser. No. 62/205,893, filed on Aug. 17, 2015, which is incorporated by reference in its entirety.

GOVERNMENT INTEREST

This invention was made with United States government support under grant number 1R43GM100638, which was awarded by the National Institutes of Health. The United States government has certain rights in this application.

BACKGROUND OF THE INVENTION

Glycosylated natural products comprise a large proportion of bioactive compounds utilized as pharmaceuticals or pursued as novel drug leads. Among these natural glycoconjugates, a majority contain deoxysugars that have one or more of their hydroxyl moieties removed and/or replaced with various functional groups. These modifications create diversity among deoxysugars and when appended to macromolecules can greatly influence their physical properties. These deoxysugars play a direct role in conferring biological activity including inhibition of DNA-processing (mithramycin and epirubicin), targeting specific proteins (staurosporine), inhibition of translation (erythromycin A), DNA-recognition (calicheamicin), inhibition of cell wall biosynthesis (vancomycin) and membrane recognition (amphotericin). This has spurred a robust interest in glycoengineering efforts to alter sugar substituents or append sugar moieties to glycosylated or non-glycosylated natural products, respectively. Unfortunately, several problems exist limiting the widespread utilization of such an approach including most notably the virtual unavailability of commercial activated deoxysugars.

As natural product secondary metabolites are ideal candidates for glycodiversification, the need for TDP-deoxysugar libraries are becoming more and more apparent. TDP-deoxysugar availability is also important for expanding the understanding of glycosyltransferase activity in secondary metabolic pathways. Glycosyltransferase activity is often indirectly evaluated by sequence comparison and inactivation experiments which delete the putative glycosyltransferase encoding gene to produce non-glycosylated natural products. To acquire in depth biochemical and mechanistic data on these important sugar transferring enzymes, in vitro analysis utilizing an aglycone (acceptor substrate) and TDP-deoxysugar (donor substrate) must be performed. Only a handful of glycosyltransferases, such as GtfC (chloroeremomycin), EryCIII (erythromycin A), AknS (aclarubicin), DesVII (neomethymycin and pikromycin), SpnG (spinosyn) and MtmGIV (mithramycin) have been characterized utilizing their natural TDP-deoxysugar donor substrate, which were all made through complex synthetic or chemoenzymatic preparations. Losey et al., *Biochemistry* 2001, 40, 4745; Yuan et al., *J Am Chem Soc* 2005, 127, 14128; Leimkuhler et al., *J Am Chem Soc* 2007, 129, 10546; Borisova et al., *J Am Chem Soc* 2004, 126, 6534; Chen et al. *J Biol Chem* 2009, 284, 7352; Wang et al., *Angew Chem Int Ed Engl* 2012, 51, 10638.

In general, chemical synthesis or chemoenzymatic synthesis are not suitable approaches for commercial production of heavily modified TDP-deoxysugars due to several step synthetic procedures and poor overall yields. Activated TDP-deoxysugars are largely provided through analytical scale synthetic or chemoenzymatic preparations and most are completely unavailable through commercial sources. A system for the preparation of TDP-deoxysugars, therefore, has extraordinary applicability in providing rare materials for glycoscience research and the development of innovative new therapeutics.

SUMMARY OF THE INVENTION

In an embodiment the invention provides a recombinant microorganism comprising:
(a) a functional deletion of rmlC (dTDP-4-dehydrorhamnose 3,5-epimerase), rmlD (dTDP-4-dehydrorhamnose reductase), wecE (TDP-4-oxo-6-deoxy-D-glucose transaminase), and wecD (TDP-fucosamine acetyltransferase); and
(b) a recombinant polynucleotide encoding rmlA (glucose-1-phosphate thymidylyltransferase), rmlB (dTDP-glucose 4, 6-dehydratase), pgm (phosphoglucomutase), or combinations thereof.

The recombinant microorganism can further comprise:
(c) a functional deletion of one or two of:
(i) pgi (glucose-6-phosphate isomerase),
(ii) zwf (glucose-6-phosphate 1-dehydrogenase), and
(iii) ptsG (PTS system glucose-specific transporter).

A recombinant microorganism can have a functional deletion of wecE (TDP-4-oxo-6-deoxy-D-glucose transaminase), a functional deletion of wecD (TDP-fucosamine acetyltransferase), a functional deletion of rmlC (dTDP-4-dehydrorhamnose 3,5-epimerase), a functional deletion of zwf (glucose-6-phosphate 1-dehydrogenase) and a recombinant polynucleotide encoding rmlA (glucose-1-phosphate thymidylyltransferase).

A recombinant microorganism can have a functional deletion of wecE (TDP-4-oxo-6-deoxy-D-glucose transaminase), a functional deletion of wecD (TDP-fucosamine acetyltransferase), a functional deletion of rmlC (dTDP-4-dehydrorhamnose 3,5-epimerase), and a recombinant polynucleotide encoding rmlA (glucose-1-phosphate thymidylyltransferase).

A recombinant microorganism can further comprise one or more recombinant polynucleotides that encode one or more proteins necessary for production or expression of one or more TDP-deoxysugars.

A recombinant microorganism can comprise one or more recombinant polynucleotides that encode fcf1, fcf2, kijD10, oleW, con8, simB5, chlC5, rmlC, novU, novS, novW, gerF, gerKI, megDII, evaB, dvaC, evaC, evaD, hedK, evaE, hedI, kijB1, oleV, med14, hedN, med15, hedH, staE, megDIV, staK, aknL, dnmU, aclM, dnmV, spnQ, urdQ, slgS7, slgS5, urdZ1, sig5, urdZ3, spnR, spnS, desVI, desI, desII, megCIV, desV, megDII, megDIII, megDV, msgDV, tyl1A, tylB, tylMI, spnO, spnN, staE, rmlC, megCV, or combinations thereof.

A recombinant microorganism can produce one or more of the following TDP-deoxysugars: TDP-D-fucose, TDP-D-fucofuranose, TDP-D-olivose, TDP-L-rhamnose, TDP-L-noviose, TDP-L-eremosamine, TDP-D-forosamine, TDP-N, N-didemethyl-D-forosamine, TDP-D-desosamine, TDP-4-amino-D-quinovose, or TDP-N, N-didemethyl-D-desosamine.

A recombinant microorganism can further comprise a functional deletion of one or more of galU (glucose-1-phosphate uridylyltransferase), galT (galactose-1-phosphate uridylyltransferase), and glgC (glucose-1-phosphate adenylyltransferase).

A recombinant microorganism can further comprise a recombinant polynucleotide encoding cytosolic adenylate kinase 1 (AK1), a recombinant polynucleotide encoding ribonucleotide reductase (NrdAB), a recombinant polynucleotide encoding a mutant ribonucleotide reductase (NrdA$_{H59A}$B), or combinations thereof.

A recombinant microorganism can further comprise a recombinant glycosyltransferase polynucleotide.

The recombinant microorganism can be *Escherichia coli*.

Another embodiment of the invention provides a method of producing a TDP-deoxysugar comprising culturing recombinant microorganism in culture medium comprising glucose, fructose, gluconate, glycerol, or combinations thereof, under conditions suitable for conversion of glucose, fructose, gluconate, glycerol, or combinations thereof to a TDP-deoxysugar, and isolating the TDP-deoxysugar. The production of the TDP-deoxysugar can be increased as compared to a corresponding microorganism lacking the functional deletions and recombinant polynucleotides of the recombinant bacterium when cultured under the same conditions.

Still another embodiment of the invention provides a method of producing a glycosylated TDP-deoxysugar comprising culturing a recombinant microorganism of the invention having a recombinant glycosyltransferase polynucleotide in culture medium comprising glucose, fructose, gluconate, glycerol, or combinations thereof, under conditions suitable for conversion of glucose, fructose, gluconate, glycerol, or combinations thereof to a glycosylated TDP-deoxysugar, and isolating the glycosylated TDP-deoxysugar. One or more aglycones can be added to the culture medium.

Yet another embodiment provides a method of producing a glycosylated TDP-deoxysugar comprising contacting an isolated TDP-deoxysugar produced from a recombinant microorganism of the invention with a glycosyltransferase and an aglycone under suitable reaction conditions and isolating the glycosylated TDP-deoxysugar from the reaction mixture.

A versatile system has been developed to produce thymidine diphosphate (TDP) activated deoxysugars including di- and tri-deoxysugars, amino sugars and branched-chain sugars. These specialized activated hexoses are primarily utilized during the biosynthesis of plant and microbial secondary metabolites, where they are appended to an acceptor substrate through glycosyltransferase (GT) activity. The resulting deoxysugar residues are often found to play a crucial role in conferring biological activity to their respective aglycone, and have become an ideal derivatization point (glycodiversification) for the development of novel bioactive compounds including cardioglycosides, antibiotics and anticancer therapeutics.

Provided herein are recombinant microorganisms with increased TKDG (TDP-4-keto-6-deoxy-D-glucose; a key intermediate of TDP-deoxysugars) production and accumulation through increased glucose flux toward polysaccharide biosynthesis and the removal of endogenous TDP-deoxysugar pathways. The TKDG overproducing microorganisms can then be used in conjunction with exogenous deoxysugar biosynthetic enzymes to produce specific TDP-deoxysugars.

BRIEF DESCRIPTION OF THE DRAWINGS

FIG. 1 Shows the pathway for the production of TDP-4-keto-6-deoxy-D-glucose (TKDG).

FIG. 2 shows a metabolically engineered strain with increased production and accumulation of TDP-4-keto-6-deoxy-D-glucose (TKDG).

FIG. 3 shows HPLC traces of zucM01-zucM71 showing TKDG accumulation. Traces are labeled 01-71, respectively.

FIG. 6 panels A and B show plasmids for integration of pathways into genome.

DETAILED DESCRIPTION OF THE INVENTION

Figure 4:
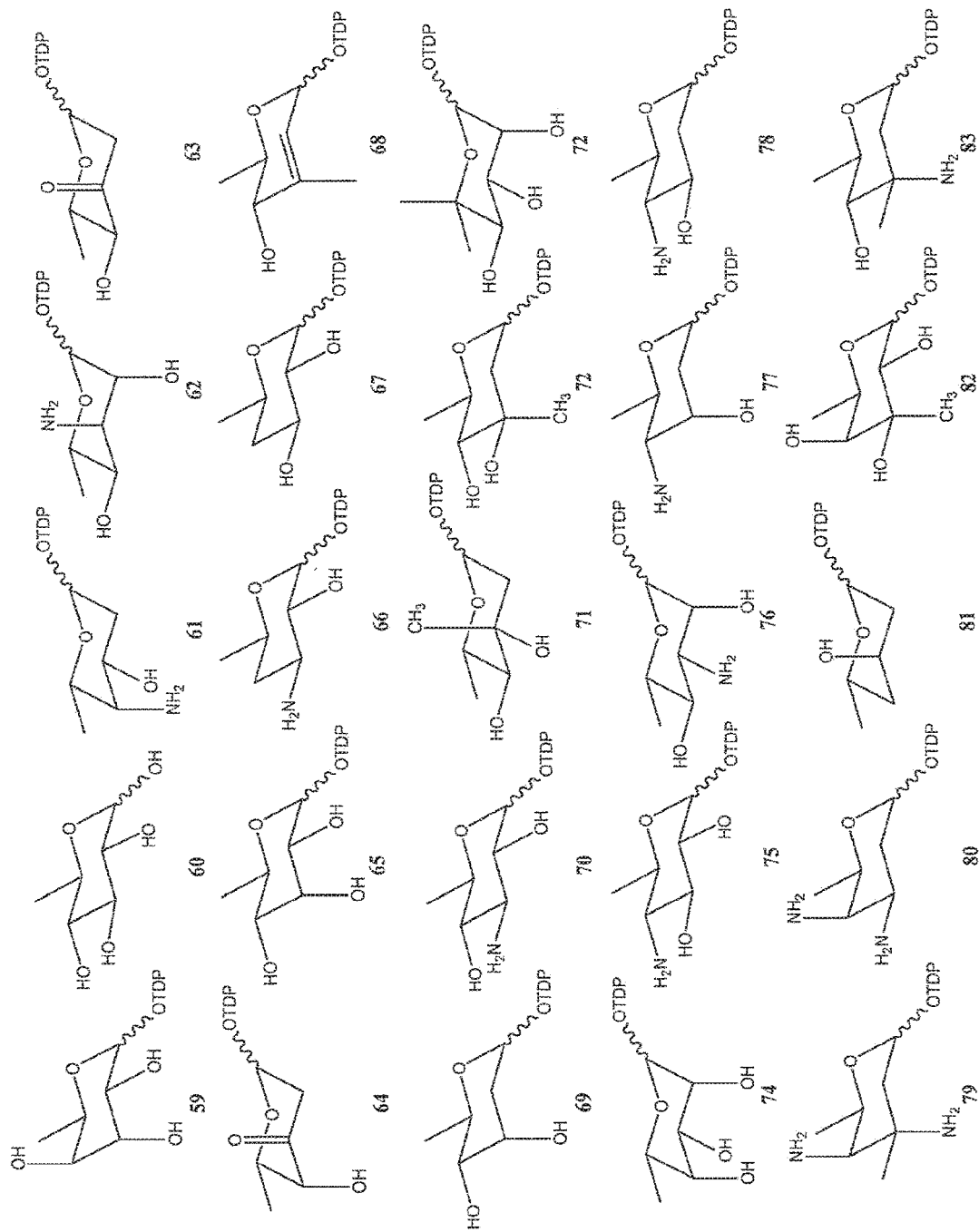
FIG. 4 shows TDP-deoxysugars utilized in nature. The sugars can be a and/or β linked TDP-deoxysugars.
Figure 4:
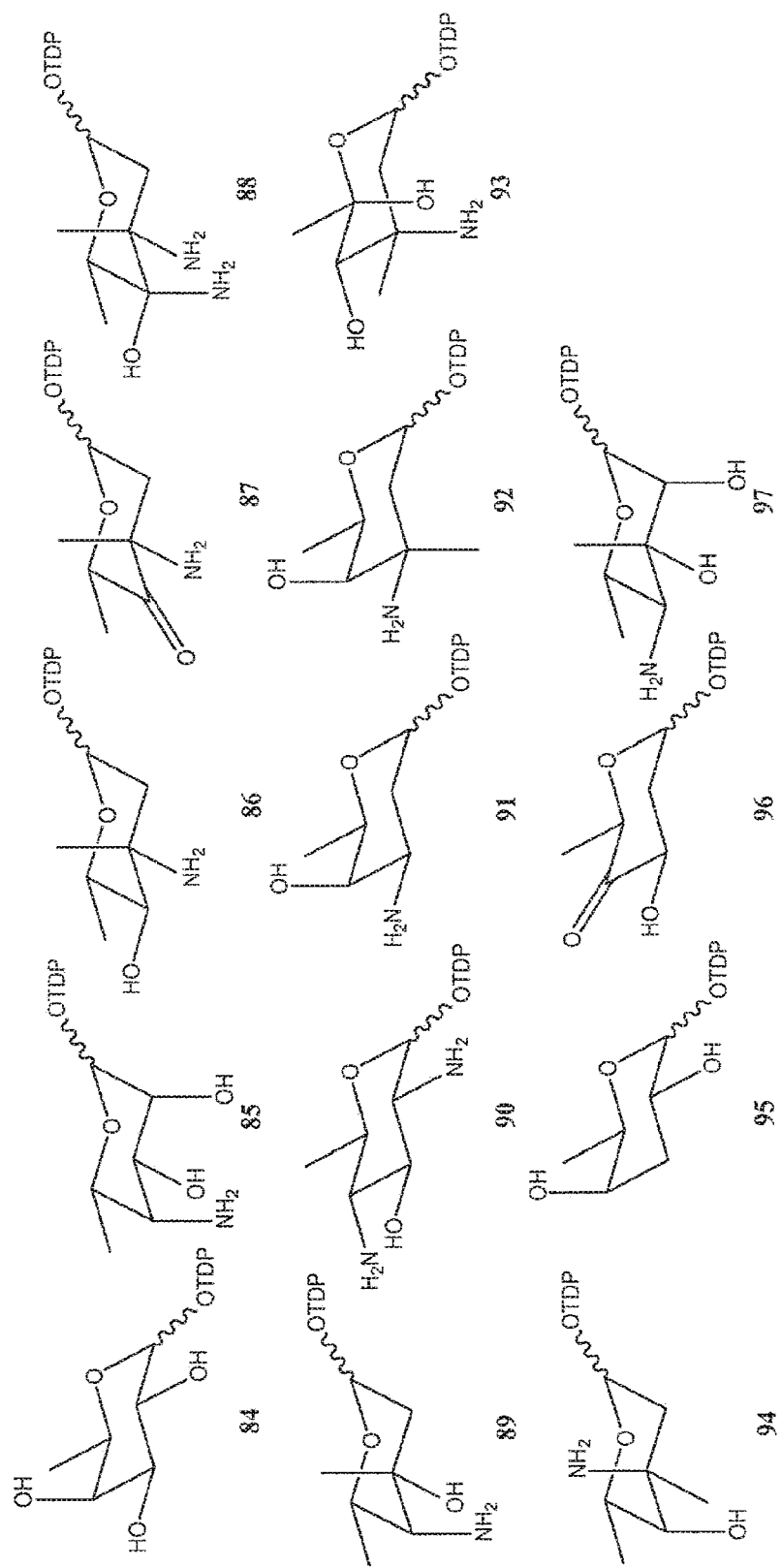

An embodiment provides methods to produce specific TDP-deoxysugars using recombinant microbes that accumulate the TDP-deoxysugar intermediate TDP-4-keto-6-deoxy-D-glucose (TKDG). An embodiment provides *E. coli* or other suitable bacteria, fungi or yeast as whole cell biocatalysts for the production of a wide variety of TDP-deoxysugars.

Increased intracellular accumulation of TKDG can be accomplished, for example by disrupting TKDG consuming pathways, such as TDP-D-Fuc4NAc, TDP-D-Qui4Nac, and the TDP-L-rhamnose pathways ((3); FIG. 2). Intracellular accumulation of glucose-6-phosphate, a precursor of TKDG, can be increased up to 30 fold by inactivating phosphoglucose isomerase (pgi), glucose-6-phosphate dehydrogenase (zwf), and/or pstG from the glycolytic and pentose phosphate pathways, respectively (FIG. 2).

*E. coli* and other microorganisms can be used as whole-cell biocatalysts for the production of TDP-deoxysugars. This approach is advantageous compared to chemical synthetic and chemoenzymatic routes of preparing TDP-deoxysugars in several ways including:

1. No need for activation chemistry as the microorganisms can activate glucose-1-phosphate utilizing endogenous TDP-deoxysugar pathway enzymes.
2. Utilizes inexpensive glucose as the starting material by hijacking the natural metabolic pathway of TDP-deoxysugars.
3. Microorganisms can provide TTP and all co-factors, which removes the need for regeneration systems to prepare TTP and ATP as in chemoenzymatic approaches.
4. Versatility to make several deoxysugars by creating individual strains that produce the TKDG intermediate, which serves as a branching point for all TDP-deoxysugars.

TDP-Deoxysugars and Bioactive Compounds.

TDP-deoxysugars are a class of thymidine diphosphate activated hexoses that are almost exclusively found to be deoxygenated in at least the C6 position of the pyranose ring. Many are further deoxygenated at the C-2, C-3 or C-4 positions and can be additionally modified to contain various functional groups creating structural diversity unmatched by other classes of activated sugars. In bacteria, TDP-deoxysugars are derived from glucose-6-phosphate (G6P) and lead to TDP-4-keto-6-deoxy-D-glucose (TKDG), the branching point for all TDP-deoxysugars. This 6-deoxy intermediate is further modified by a surprisingly small number of functionally distinct regio- and stereospecific deoxysugar enzymes including epimerases, dehydratases, methyltransferase, am inotransferases, acyltransferases, and ketoreductases which drive TDP-deoxysugar structural diversity.

The most prolific source of heavily modified TDP-deoxysugars are found in actinomycetes, a group of soil dwelling bacteria rich in secondary metabolite production. See FIG. 1.

TDP-Deoxysugar Pathways in E. Coll.

*E. coli* utilize unusual sugars, including TDP-deoxysugars, in lipopolysaccharide and enterobacterial common antigen biosynthesis which serve as important structural features including a source of chemical cell-surface diversity among Enterobacteriaceae. Specifically, in route to polysaccharide biosynthesis the sugar phosphotransferase system (PTS) is utilized by *E. coli* to transport and phosphorylate glucose to produce glucose-6-phosphate (G6P). Several primary metabolic pathways utilize G6P including polysaccharide biosynthesis, glycolysis and the pentose phosphate pathway. The phosphoglucose mutase encoding pgm diverts G6P to polysaccharide biosynthesis by forming glucose-1-phosphate which is activated by a thymidylyltransferase (RmlA) which forms TDP-D-glucose. 6-deoxygenation of TDP-D-glucose by RmlB, a TDP-D-glucose-4,6-dehydratase, results in TKDG and is further modified according to specific deoxysugar pathways (FIG. 2). *E. coli* AB707 is a wild-type K-12 strain that does not produce O-specific side chain lipopolysaccharides due to mutations in the O-antigen rml gene cluster. Despite the lack of O-antigen, *E. coli* K-12 harbors all TDP-L-rhamnose biosynthetic genes including RmlC (3,5-epimerase) and RmlD (4-ketoreductase), but not genes for TDP-D-Qui4NAc (vio) biosynthesis. In addition to TDP-L-rhamnose, *E. coli* AB707 produces TDP-D-Fuc4NAc for enterobacterial common antigen synthesis. TDP-D-Fuc4NAc is formed from TKDG through the catalytic action of WecE (transaminase) and WecD (acyltransferase).

Combining genetic modifications that individually accumulate G6P (Δpgi, zwf, pstG) or TKDG (ΔrmlC, rmlD, wecC, wecD) with the overexpression of TKDG biosynthetic enzymes (RmlA and RmlB) results in significantly increased production of the TDP-deoxysugar intermediate TKDG. These genetically modified strains can then be used to produce various TDP-deoxysugars using exogenous deoxysugar biosynthetic genes that can then convert the resulting TKDG pool into specific TDP-deoxysugars.

Recombinant Microorganisms

Microorganisms include, for example, bacteria such as *Escherichia coli, Streptomyces* sp., *Streptomyces niveus, Streptomyces neyagawaensis, Streptomyces antibioticus, Streptomyces niveus, Streptomyces* sp. KCTC, *Streptomyces griseoruber, Streptomyces* sp. AM-7161, *Streptomyces* sp. TP-A0274, *Streptomyces galilaeus, Streptomyces peucetius, Streptomyces fradiae, Streptomyces lydicus, Streptomyces venezuelae*, fungi, and yeasts such as *Saccharomyces* sp., *Saccharomyces cerevisiae, Pichia* sp., *Pichia pastoris*, and *Pichia angusta*.

Microorganisms can be recombinant. Recombinant microorganisms have undergone genetic engineering. Genetic engineering means that one or more nucleic acids of the microorganism have been altered by the: introduction of new nucleic acids (via, for example, transformation, phage introduction, electroporation, microinjection of nucleic acids, and others), the deletion of nucleic acids, or other manipulation of nucleic acids. Recombinant microorganisms are not naturally occurring.

In an embodiment one, two, or three of pgi (glucose-6-phosphate isomerase) (e.g. GenBank EGT70493.1, P0A6T1.1, B6I5N7.1, A8A7C4.1), zwf (glucose-6-phosphate 1-dehydrogenase) (e.g., GenBank ANK01823.1, CUU94006.1, AAA57023.1, AAA24775.1), and ptsG (PTS system glucose-specific transporter) (e.g., GenBank ACZ37324.1, ACZ37323.1, ACZ37322.1, ACZ37320.1) are functionally deleted through genetic engineering from the microorganism. That is the following combinations of deletions can be present: deletion of pgi; pgi and zwf; pgi and ptsG; zwf; zwf and ptsG; ptsG; or ptsG, zwf, and pgi. Alternatively, one, two, or three of pgi, zwf, and ptsG are naturally absent or naturally non-functional in the microorganism. In an embodiment, one or more of rmlC (dTDP-4-dehydrorhamnose 3,5-epimerase) (e.g., GenBank AAC63615.1, AAT85650.1, ALC76394.1, AFC91454.1, AFC91441.1, AFC91428.1), rmlD (dTDP-4-dehydrorhamnose reductase) (e.g. GenBank AAC63613.1, ADC54933.1, ACH97128.1, ACD37175.1, ACD37167.1), wecE (TDP-4-oxo-6-deoxy-D-glucose transaminase) (e.g., GenBank AKF74090.1, AKF69952.1, AKF65812.1, AKF61673.1), wecD (TDP-fucosamine acetyltransferase) (e.g., GenBank EGT71046.1, AKF74089.1, AKF69951.1, AKF65811.1, AKF61672.1), and combinations thereof are functionally deleted through genetic engineering from the microorganism. Alternatively, one, two, three, or four of rmlC, rmlD, wecE, wecD, and combinations thereof are naturally absent or naturally non-functional in the microorganism.

Functionally deleted, functional deletion, or non-functional means that a sufficient amount of the gene region is removed, changed, or otherwise damaged, e.g., by natural mutation, induced mutation, or genetic engineering modification, so that the gene region is no longer capable of producing substantial amounts of functional products of gene expression or the gene region is not able to otherwise produce products of gene expression that perform their normal function. In an embodiment a functional deletion results in 10, 5, 4, 3, 2, 1% or less expression of functional products of gene expression as compared to a corresponding microorganism without the functional deletion. In other embodiments a functional deletion results in expression of no functional products of gene expression as compared to a corresponding microorganism without the functional deletion. If desired, part of the gene region can be removed, or the entire gene region can be removed. Mutation of the gene region by addition or substitution can also be useful to functionally delete a gene region. A functional deletion can be a naturally occurring functional deletion (e.g., a naturally occurring mutation that results in a functional deletion) or a genetically engineered functional deletion. A microorganism can comprise only genetically engineered functional deletions, only naturally occurring functional deletions, or combinations of genetically engineered functional deletions and naturally occurring functional deletions.

In an embodiment, a microorganism comprises a recombinant polynucleotide encoding rmlA (glucose-1-phosphate thymidylyltransferase) (e.g., GenBank AKH33672.1, CCC20149.1, AAV60878.1, AAV62789.1), rmlB (dTDP-glucose 4, 6-dehydratase) (e.g., GenBank CCC20147.1, AAV60876.1, AAV62787.1), pgm (phosphoglucomutase) (e.g., GenBank AAL35381.1, CCC19955.1, ALX91952.1, ALX91101.1, ALX90607.1), or combinations thereof such that functional rmlA, rmlB, or pgm proteins are expressed. In an embodiment, rmlA, rmlB, and pgm polynucleotides are from *Streptococcus thermophilus*. A recombinant polynucleotide is a polynucleotide that is provided to the microorganism by one or more genetic engineering methods. A microorganism comprising a recombinant polynucleotide is not a naturally occurring microorganism.

In some embodiments, a recombinant microorganism can further comprise a functional deletion of one or more of galU, glgC, and galT.

A recombinant microorganism can further comprise a recombinant polynucleotide encoding cytosolic adenylate kinase 1 (AK1), a recombinant polynucleotide encoding ribonucleotide reductase (NrdAB), a recombinant polynucleotide encoding a mutant ribonucleotide reductase (NrdA$_{H59A}$B), or combinations thereof.

In some embodiments a recombinant microorganism, such as *E. coli*, accumulates or produces 5, 10, 20, 30, 40, 50, 60, 70, 80, 90, 95% or more TKDG than a corresponding microorganism that does not comprise the functional deletions or recombinant polynucleotides of the recombinant microorganism. In some embodiments a recombinant microorganism, such as *E. coli*, accumulates or produces 2, 3, 4, 5, 6, 7, 8, 9, 10 or more mg/L of TKDG.

A microorganism can further comprise one or more recombinant polynucleotides for expression of one or more TDP-deoxysugars. These polynucleotides encode one or more proteins necessary for the production of one or more TDP-deoxysugars by the microorganism. These polynucleotides can comprise, for example, fcf1 (from, e.g., *E. coli*), fcf2 (from e.g., *E. coli*), kijD10 (from, e.g., *Actinomadura kijaniata*), oleW (from, e.g., *Streptomyces niveus*), con8 (from, e.g., *Streptomyces neyagawaensis*), simB5 (from, e.g., *Streptomyces antibioticus*), chlC5 (from, e.g., *Streptomyces antibioticus*), rmlC (from, e.g., *Escherichia coli*), novU (from, e.g., *Streptomyces niveus*), novS (from, e.g., *Streptomyces niveus*), novW (from, e.g., *Streptomyces niveus*), gerF (from, e.g., *Streptomyces* sp. KCTC), gerKI (from, e.g., *Streptomyces* sp. KCTC), evaB (from, e.g., *Amycolatopsis orientalis*), dvaC (from, e.g., *Amycolatopsis balhimycina*), evaC (from, e.g., *Amycolatopsis orientalis*), evaD (from, e.g., *Amycolatopsis orientalis*), hedK (from, e.g., *Streptomyces griseoruber*), evaE (from, e.g., *Amycolatopsis orientalis*), hedI (from, e.g., *Streptomyces griseoruber*), kijB1 (from, e.g., *Actinomadura kijaniata*), oleV (from, e.g., *Streptomyces antibioticus*), med14 (from, e.g., *Streptomyces* sp. AM-7161), hedN (from, e.g., *Streptomyces griseoruber*), med15 (from, e.g., *Streptomyces* sp. AM-7161), hedH (from, e.g., *Streptomyces griseoruber*), megDIV (from, e.g., *Micromonospora meglomicea*), staK (from, e.g., *Streptomyces* sp. TP-A0274), aknL (from, e.g., *Streptomyces galilaeus*), dnmU (from, e.g., *Streptomyces peucetius*), aclM (from, e.g., *Streptomyces galilaeus*), dnmV (from, e.g., *Streptomyces peucetius*), spnQ (from, e.g., *Saccharopolyspora spinosa*), urdQ (from, e.g., *Streptomyces fradiae*), slgS7 (from, e.g., *Streptomyces niveus*), slgS5 (from, e.g., *Streptomyces lydicus*), urdZ1 (from, e.g., *Streptomyces fradiae*), urdZ3 (from, e.g., *Streptomyces fradiae*), spnR (from, e.g., Saccharopolyspora *spinosa*), spnS (from, e.g., Saccharopolyspora *spinosa*), desVI (from, e.g., *Streptomyces venezuelae*), desI (from, e.g., *Streptomyces venezuelae*), desII (from, e.g., *Streptomyces venezuelae*), megCIV (from, e.g., *Saccharopolyspora erythraea* NRRL2338), desV (from, e.g., *Streptomyces venezuelae*), megDII (from, e.g., *Micromonospora meglomicea*), megDIII (from, e.g., *Micromonospora meglomicea*), megDV (from, e.g., *Micromonospora meglomicea*), tyl1A (from, e.g., *Streptomyces fradiae*), tylB (from, e.g., *Streptomyces fradiae*), tylMI (from, e.g., *Streptomyces fradiae*), spnO (from, e.g., *Saccharopolyspora spinosa*), spnN (from, e.g., *Saccharopolyspora spinosa*), staE (from, e.g., *Streptomyces* sp. TP-A0274), rmlC (from, e.g., *Escherichia coli*), megCV (from, e.g., *Saccharopolyspora erythraea* NRRL2338), or combinations thereof. Sequences of these polynucleotides and corresponding polypeptides are readily available in gene databases such as UniProt or GenBank and are otherwise known in the art.

Methods of Producing TDP Deoxysugars

In an embodiment, methods of producing one or more TDP-deoxysugars are provided. The methods can comprise culturing a recombinant microorganism in culture medium comprising glucose, fructose, gluconate, glycerol, or combinations thereof, under conditions suitable for conversion of glucose, fructose, gluconate, glycerol, or combinations thereof to a TDP-deoxysugar. The production of TDP-deoxysugars by the recombinant microorganism is increased as compared to a corresponding microorganism lacking any functional deletions and recombinant polynucleotides of the recombinant microorganism, when cultured under the same conditions. A corresponding microorganism is of the same species and genus of the recombinant microorganism. For example, the amount of TDP-deoxysugars provided by recombinant microorganisms disclosed herein can be about 5, 10, 20, 30, 40, 50, 60, 70, 80, 90, 95, 97, 98, 99% or more than corresponding microorganisms, wild-type microorganisms or microorganisms not having the genetic modifications described herein.

The one or more TDP-deoxysugars can accumulate extracellularly or intracellularly. In embodiments the TDP-deoxysugars are soluble. The one or more TDP-deoxysugars can be isolated from cell culture medium or from the cells of the recombinant microorganism.

Production of any TDP-Deoxysugars or TDP-Deoxysugar Intermediate.

Based on these methods it is possible to produce any TDP-deoxysugar or TDP-deoxysugar intermediate as long as an active protein is expressed for each biosynthetic step. A comprehensive study of naturally occurring deoxysugars was recently published. See Elshahawi et al., *Chem Soc Rev* 2015. From this study over 90 deoxysugars were identified (FIG. 4). These include TDP-D-spectinose (9), TDP-L-rhodinose (10), TDP-L-ristosamine (11), TDP-L-rhamnose (12), TDP-D-oliose (13), TDP-D-amicetose (14), TDP-L-oliose (15), TDP-L-rednose (16), TDP-L-cinerulose (17), TDP-L-aculose (18), TDP-D-kerriose (19), TDP-D-rhodinose (20), TDP-D-boivinose (21), TDP-D-angolosamine (22), TDP-4-epi-L-tolyposamine (23), TDP-6-deoxy-L-altrose (24), TDP-N,N-didemethyl-D-forosamine (25), TDP-D-mycarose (26), TDP-3-epi-4-epi-L-vancosmine (27), TDP-3-amino-2,3,6-trideoxy-L-glucose (28), TDP-L-daunosamine (29), TDP-L-digitoxose (30), TDP-D-ristosamine (31), TDP-3-amino-3,6-dideoxy-L-talose (32), TDP-D-fucuofuranose (33), TDP-4-hydroxy-D-fucofuranose (34), TDP-D-virenose (35), TDP-D-ravidosamine (36), TDP-4-keto-D-virenose (37), TDP-4-amino-4,6,-dideoxy-D-allose (38), TDP-D-fucosamine (39), TDP-L-mycarose (40), TDP-4-amino-2,4-dideoxy-L-fucose (41), TDP-3-keto-4-C-methyl-D-fucose (42), TDP-L-amicetose (43), TDP-D-cinerulose (44), TDP-4-deoxy-L-daunosamine (45), TDP-L-olivose (46), TDP-2,6-dideoxy-L-glucose (47), TDP-3-C-methyl-L-rhamnose (48), TDP-L-avidinosamine (49), TDP-4-amino-2,3,4,6-tetradeoxy-L-glucose (50), TDP-L-vancosamine (51), TDP-4-epi-L-mycarose (52), TDP-L-actinosamine (53), TDP-6-deoxy-L-talose (54), TDP-4-keto-L-olivose (55), TDP-D-digitoxose (56), TDP-4-keto-D-mycarose (57), TDP-4-hydroxy-D-olivose (58), TDP-6-deoxy-D-gulose (59), TDP-D-quinovose (60), TDP-4-amino-2,4,6-trideoxy-L-galactose (61), TDP-3-amino-3,6-dideoxy-L-altrose (62), TDP-3-keto-2,3,6-trideoxy-L-glucose (63), TDP-2-deoxy-3-keto-L-fucose (64), TDP-6-deoxy-D-allose (65), TDP-N,N-didemethyl-d-desosamine (66), TDP-4-deoxy-D-fucose (67), TDP-3-C-methyl-2,3,6-trideoxy-2,3-unsaturated-D-glucose (68), TDP-2,6-dideoxy-D-altrose (69), TDP-N,N-didemethyl-D-mycaminose (70), TDP-L-chromose (71), TDP-D-olivomicose (72), TDP-L-noviose (73), TDP-6-deoxy-L-talose (74), TDP-D-quinovosamine (75), TDP-L-mycosamine (76), TDP-N-desmethyl-D-vicenisamine (77), TDP-D-pyrrolosamine (78), TDP-3,4-diamino-3-C-methyl-2,3,4,6-tetradeoxy-D-gulose (79), TDP-3,4-diamino-2,3,4,6-tetradeoxy-D-galactose (80), TDP-4-deoxy-L-digitoxose (81), TDP-D-elsarose (82), TDP-D-saccharosamine (83), TDP-D-fucose (84), TDP-4-amino-4,6-dideoxy-L-talose (85), TDP-4-epi-L-vancosamine (86), TDP-4-keto-L-vancosamine (87), TDP-4-C-amino-4-epi-L-vancosamine (88), TDP-4-amino-4-deoxy-3-C-methyl-L-fucose (89), TDP-2,4-diamino-2,4,6-trideoxy-D-glucose (90), TDP-3-amino-2,3-dideoxy-D-fucose (91), TDP-D-vancosamine (92), TDP-3-epi-4-epi-5-hydroxy-D-vancosamine (93), TDP-3-epi-L-vancosamine (94), TDP-3-deoxy-D-fucose (95), TDP-4-keto-D-olivose (96) and TDP-L-sibirosamine (97). Any of these TDP-deoxysugars can be produced by the methods disclosed herein.

Furthermore, TDP-deoxysugars produced by methods disclosed herein can comprise common modifications such as O- or N-methylations or acetylations. In addition to being able to produce these products, it is also possible to produce intermediates in these pathways such as keto-sugar intermediates. Moreover, these methods can be used as a powerful combinatorial tool to produce unusual and unique TDP-deoxysugars by combining various genes in unnatural combinations.

Additional Improvements of TDP-Deoxysugar Production

A portion of the genetic engineering work in Example 1 was aimed at minimizing G6P metabolism through pathways other than polysaccharide biosynthesis. This was accomplished by deleting pgi (zucM61) or pgi and zwf (zucM71) to block glycolysis and glycolysis plus the pentose phosphate pathway, respectively. These deletions increased TKDG yields demonstrating an increase in G6P consumption toward TDP-deoxysugars. In these experiments zucM61 produced higher product yields than zucM71 even though zucM71 was blocked in both glycolysis and the pentose phosphate pathway. In an embodiment, a microorganism can have a functional deletion of only zwf (and not of pgi and ptsG).

The double pgi, zwf mutant (zucM71) did not result in the highest production of TDP-deoxysugars. The inability of zucM71 to grow on glucose minimal media clearly demonstrates the successful blocking of glucose through glycolysis and pentose phosphate pathways. This indicates that glucose consumption in zucM71 accumulates G6P and proceeds to polysaccharide biosynthesis via phosphoglucomutase (Pgm) activity resulting in G1P (FIG. 2). There are several enzymes that utilize G1P including GalU (glucose-1-phosphate uridylyltransferase) (e.g. GenBank EHU90746.1, ANK06855.1, EHU26419.1, ALY13246.1), GalT (galactose-1-phosphate uridylyltransferase) (e.g. GenBank EGT66884.1, ANK06111.1, CUU92753.1, CCQ27651.2), and GlgC (glucose-1-phosphate adenylyltransferase) (e.g., GenBank CAA23544.1, EGT69433.1, EFI18112, EFE98859.1) for UDP- and ADP-sugar formation for polysaccharide and glycogen synthesis, respectively. See Kamogawa & Kurahashi, *J Biochem* 1965, 57, 758, Arabshahi et al., *Biochemistry* 1986, 25, 5583, Ballicora et al., *Microbiol Mol Biol Rev* 2003, 67, 213.

Deletions of these genes can prevent the loss of G1P thereby increasing the G1P pool for RmlA to produce TDP-D-glucose.

Some embodiments provide a microorganism further comprising functional deletions of one or more of galU, glgC, and galT. For example, a microorganism, such as *E. coli*, can have functional deletions of wecE and wecD, a functional deletion of rmlC, a functional deletion of pgi, a recombinant polypeptide that encodes rmlA, and one or more functional deletions of galU, glgC, or galT. In another embodiment a microorganism can have a function deletion of wecE and wecD, a functional deletion of rmlC, a functional deletion of pgi, a functional deletion of zwf, a recombinant polypeptide that encodes rmlA, and one or more functional deletions of galU, glgC, or galT.

The activation of glucose-1-phosphate in route to TDP-deoxysugars can be accomplished by coupling with TTP via RmlA (FIG. 2). A limited number of studies have quantitated nucleoside triphosphates pools in *E. coli*; however, TTP pools are maximal at 256 µM (123 mg/L) in mid-log phase and then oscillate downward throughout stationary growth. See Buckstein et al., *J Bacteriol* 2008, 190, 718. This limited TTP pool, shared between DNA synthesis and polysaccharide synthesis, can be a bottleneck for TDP-deoxysugar production. Two strategies to alleviate this problem include 1) overexpression of chicken cytosolic adenylate kinase 1 (AK1) and/or 2) overexpression of *E. coli* ribonucleotide reductase (NrdAB).

Adenylate kinase (AK1) from chicken (e.g., GenBank BAA00182.1) typically catalyzes ATP formation, but was found to also produce TTP from TDP and ADP. See Tanizawa et al., *J Biochem* 1987, 101, 1289. The overexpression of AK1 in *E. coli* has been shown to give a ~10 fold increase in TTP concentration compared to control strains. See Shioda et al., *Biochim Biophys Acta* 1991, 1115, 36. Alternatively, NrdAB is involved in deoxyribonucleotide production and was found to be up-regulated during exposure to UV. See et al., *Proc Natl Acad Sci USA* 2011, 108, 19311. This DNA-damage dependent up-regulation of NrdAB is linked to increased dNTP pools. NrdAB converts ribonucleotides (ADP, UDP, GDP and CDP) to deoxyribonucleotides (dADP, dUDP, dGDP and dCDP), but is not directly involved in TTP production. Thelander & Reichard, P. *Annu Rev Biochem* 1979, 48, 133.

Instead the elevated levels of dUDP and dCDP from NrdAB overexpression are metabolized to dUMP which is eventually converted to TTP. Similar to AK1, NrdAB overexpression was found to increase TTP pools ~3-8 fold. The max TTP pools were found when a mutant of NrdAB (NrdA$_{H59A}$B) was used which removed feedback inhibition by dATP. See Gon et al., *Proc Natl Acad Sci USA* 2011, 108, 19311.

Therefore, microorganisms can further comprise a recombinant polynucleotide encoding cytosolic adenylate kinase 1 (AK1) polynucleotide, a recombinant polynucleotide encoding ribonucleotide reductase (NrdAB), a recombinant polynucleotide encoding a mutant ribonucleotide reductase (NrdA$_{H59A}$B), or combinations thereof. For example, a microorganism can have functional deletions of wecE and wacD, a functional deletion of rmlC, a functional deletion of pgi, a recombinant polypeptide that encodes rmlA, and a recombinant polynucleotide encoding cytosolic adenylate kinase 1 (AK1), a recombinant polynucleotide encoding ribonucleotide reductase (NrdAB), a recombinant polynucleotide encoding a mutant ribonucleotide reductase (NrdA$_{H59A}$B), or combinations thereof. In another embodiment a microorganism can have a function deletion of wecE and wecD, a functional deletion of rmlC, a functional deletion of pgi, a functional deletion of zwf, a recombinant polypeptide that encodes rmlA, and a recombinant polynucleotide encoding cytosolic adenylate kinase 1 (AK1), a recombinant polynucleotide encoding ribonucleotide reductase (NrdAB), a recombinant polynucleotide encoding a mutant ribonucleotide reductase (NrdA$_{H59A}$B), or combinations thereof.

Enhancements to TDP-deoxysugar production can also achieved through fermentation optimization. These include optimization of variables such as aeration, temperature, induction time, glucose concentration, inducer concentration, and media content in both shake flasks and fermenters.

In Vitro Production of Activated Sugars.

Recombinant microorganisms disclosed herein can express soluble and active TDP-deoxysugar biosynthetic proteins. These soluble proteins (e.g., glucose-1-P, glucose-1-p-thymidylytransferase, TDP-D-glucose, TDP-glucose-4,6-dehydratase, and TKDG) can be purified or partially purified from the recombinant microorganisms and used for production of TDP-deoxysugars in vitro. This can be desirable if labile TDP-deoxysugar intermediates are wanted and in vivo production does not afford an intact product.

Production of Glycosylated End Products

Purified or partially purified TDP-deoxysugars from microorganisms disclosed herein can be used directly in glycosylation reactions as donor substrates to produce glycosylated end products in vitro. One or more TDP-deoxysugars can be added to a suitable reaction mixture containing, for example, a purified glycosyltransferase, 50 mM sodium phosphate buffer (pH 7.5), 5 mM MgCl$_2$ and an appropriate acceptor substrate (an aglycone). Glycosytransferases include, for example, GtfC (chloroeremomycin), EryCIII (erythromycin A), AknS (aclarubicin), DesVII (neomethymycin and pikromycin), SpnG (spinosyn) and MtmGIV (mithramycin). The resulting glycosylated molecule can then be purified using standard purification procedures.

Therefore, a method is provided for making a glycosylated TDP-deoxysugar in vitro. The method comprises contacting one or more TDP-deoxysugars with a glycosyltransferase and an aglycone under suitable reaction conditions. A glycosylated TDP-deoxysugar can be purified or isolated from the reaction mixture.

Glycosylated TDP-deoxysugars can also be produced in vivo. With the addition of a gene encoding a glycosyltransferase (from e.g., E. coli or Streptomyces), TDP-deoxysugar producing strains can be used to directly produce glycosylated end products in vivo. An aglycone can be introduced into the cell through direct uptake or through permeabilization of the cells of the microorganism harboring the TDP-deoxysugar and glycosyltransferase. Glycosylated products can then be recovered through cell lysis or from the culture medium following standard purification procedures.

Therefore, a method is provided for making a glycosylated TDP-deoxysugar in vivo. The method comprises providing a microorganism of the invention capable of making a TDP-deoxysugar, which further comprises one or more recombinant polynucleotides encoding one or more glycosyltransferases. The microorganism or reaction mixture is contacted with an aglycone under suitable reaction conditions. A glycosylated TDP-deoxysugar can be purified or isolated from the reaction mixture.

EXAMPLES

Example 1. Metabolic Engineering of E. coli for the Accumulation of TKDG 1.1 Inactivation of Endogenous TDP-Deoxysugar Pathways.

A set of inactivations were designed to remove endogenous TDP-deoxysugar pathways in microbes. Endogenous sugars in E. coli AB707, for example, include TDP-D-Fuc4NAc (produced by the wec genes) and TDP-L-rhamnose (produced by the rml genes) as shown in FIG. 2. Unlike E. coli BL21, E. coli AB707 does not contain the biosynthetic genes to produce TDP-4-N-acetyl-D-quinovose. Using PCR-targeted inactivation, wecD and wecE were deleted from E. coli AB707 to produce zucM1 (Table 1). zucM1 was then used for inactivation of rmlD, rmlA and rmlC in a single step to produce zucM2. The removal of rmlD and rmlC completely removes TDP-L-rhamnose specific biosynthetic genes from E. coli AB707; however, rmlA encodes a glucose-1-phosphate thymidylyltransferase responsible for producing TDP-D-glucose, a precursor to TKDG. Due to the location of rmlA, and to reduce the amount of deletions needed, all three genes are deleted in one step. We hypothesized the presence of a second glucose-1-phosphate thymidylyltransferase, encoded by rffH, in the genome would allow for the TKDG pathway to remain intact. In light of poor TKDG production results of these strains (discussed in Example 2.2), we also independently deleted only rmlC from the rml cluster. Specifically, we started with zucM1 and deleted only rmlC, producing strain zucM5. This strain lacks the ability to produce TDP-L-rhamnose, but retains rmlD. In the production of TDP-deoxysugars involving intermediates similar to TDP-4-dehydrorhamnose rmlD will need to be deleted, but for many TDP-deoxysugar pathways, the presence of RmlD does not pose a problem. Strains zucM1, zucM2 and zucM5 were made λDE3 lysogens in order to utilize T7 expression vectors, according to manufacturer's protocol (λDE3 lysogenization kit, Novagen). The newly constructed λDE3 lysogens were designated zucM11, zucM21 and zucM51, respectively (Table 1).

1.2 Channeling Glucose to TKDG

TKDG is not naturally accumulated in microorganisms. With endogenous TDP-deoxysugar pathways removed additional inactivations were completed to funnel glucose consumption through the TDP-deoxysugar pathway. This was achieved by utilizing strains such as those created in Example 1.1 by additionally blocking glycolysis (pgi) and/or the pentose phosphate pathway (zwf). Both mutations can be created sequentially where pgi is deleted from zucM2 or zucM5 then the resulting strain (zucM3 or zucM6) is used to delete zwf, producing zucM4 or zucM7 (Table 1). Additionally, zwf was deleted from zucM5 to get zucM9. All deletions were confirmed through PCR analysis (data not shown). All prepared mutants were then made λDE3 lysogens in order to utilize T7 expression vectors, according to manufacturer's protocol (λDE3 lysogenization kit, Novagen). The newly constructed λDE3 lysogens were designated zucM31, zucM61, zucM41, zucM71 and zucM91 (Table 1).

TABLE 1

| Strain Name | (DE3) Strain Name | Strain Abbrev | Genotype |
|---|---|---|---|
| AB707 | zucM01 | AB707 | |
| ZUCM1 | zucM11 | W | ΔwecE-D |
| ZUCM2 | zucM21 | WR | ΔwecE-D ΔrmlC-A-D (This kills TKDG production. Need RmlC intact.) |
| ZUCM3 | zucM31 | WRP | ΔwecE-D ΔrmlC-A-D Δpgi |
| ZUCM4 | zucM41 | WRPZ | ΔwecE-D ΔrmlC-A-D Δpgi Δzwf |
| ZUCM5 | zucM51 | WRc | ΔwecE-D ΔrmlC |
| ZUCM6 | zucM61 | WRcP | ΔwecE-D ΔrmlC Δpgi |

TABLE 1-continued

| Strain Name | (DE3) Strain Name | Strain Abbrev | Genotype |
|---|---|---|---|
| ZUCM7 | zucM71 | WRcPZ | ΔwecE-D ΔrmlC Δpgi Δzwf |
| ZUCM8 | zucM81 | WRcPZP | ΔwecE-D ΔrmlC Δpgi Δzwf ΔptsG |
| ZUCM9 | zucM91 | WRcZ | ΔwecE-D ΔrmlC Δzwf |

These were also made as the DE3 lysogen for protein expression

1.3 Removing Catabolite Repression to Restore Blocked Metabolic Pathways.

The zucM71 strain consumes glucose comparable to that of zucM61 when grown in rich media yet produces less TDP-deoxysugar than zucM61. zucM71 may be limited in cofactor regeneration specifically in reducing equivalents with the loss of glycolysis and the pentose phosphate pathway. Even though zucM61 is blocked at pgi, glucose can still enter glycolysis through the pentose phosphate pathway or the Entner-Doudoroff pathway via glyceraldehyde-3-P. This can allow for cofactor regeneration in zucM61 but not zucM71. To overcome this limitation the bacterial phosphotransferase system (PTS) was manipulated through the deletion of ptsG in zucM71. The EIICB$^{glc}$ protein (encoded by ptsG) is the glucose-specific permease of the PTS and deleting ptsG reduces glucose consumption by 50-75% compared to wild-type strains. This may sound counterproductive, but the loss of EIICB$^{glc}$ reduces catabolite repression by glucose and allow for simultaneous uptake of carbon sources. This provides a unique opportunity for zucM71 to simultaneously consume glucose and gluconate, which restores the pentose phosphate pathway (enters as 6-phosphogluconate) and glycolysis (enters as glyceraldehyde-3-phosphate), while utilizing glucose exclusively for TDP-deoxysugar biosynthesis. The deletion of ptsG from zucM71 created zucM81 (Table 1).

1.4 Overexpression of TKDG Pathway Genes.

Overexpression of PgmA, RmlA and RmlB was tested in order to optimize glucose metabolism through the TDP-deoxysugar pathway. pgmA, rmlA and rmlB were amplified from *Streptococcus thermophilus* (ATCC) using PCR. To distinguish them from *E. coli* genes the *S. thermophilus* genes are denoted with an "ST". *Streptococcus thermophilus* was chosen because its genes can give high level of expression, stability, and activity when expressed in *E. coli*. Amplified PCR products were individually cloned into pET28a (N-His$_6$-tagged) and CDFDuet1 (for co-expression). All expressed well in *E. coli* (Table 2).

TABLE 2

Protein expression profile of *S. thermophiles* genes used in this study.

| Enzyme | Protein | Plasmid | Soluble | Inclusion Bodies | % Expression as N-term His$_6$-tag |
|---|---|---|---|---|---|
| For Channeling Glucose to TDP-sugars | | | | | |
| NT | ST_RmlA | pET28a | 40 | 60 | ++++ |
| | | CDFDuet1 | 40 | 60 | +++ |
| 4,6-DH | ST_RmlB | pET28a | 40 | 60 | ++++ |
| | | CDFDuet1 | 40 | 60 | +++ |
| Mutase | ST_PgmA | pET28a | 90 | 10 | +++ |
| | | CDFDuet1 | 90 | 10 | ++++ |

Ketoreductase (KR), Dehydratase (DH) and nucleotidyltransferase (NT)

Example 2

2.1 Monitoring TKDG and Other TDP-Deoxysugar Accumulation in Engineered Strains.

The production of TKDG at approximately 100 mg/L in mutant strains was desired to ensure that yields of up to 50 mg/L could be achieved for the final desired products. This required the ability to monitor intracellular TKDG production. Several methods were analyzed; however, we chose to modify a reported organic extraction method utilizing chloroform/methanol (1:1, v/v). See Yang et al., *Anal Biochem* 2012, 421, 691. This method was superior for quickly checking time point samples from multiple shake flasks compared to other methods for cell lysis and later extraction of TDP-deoxysugars from a cell free lysate. This method also allows for convenient concentration of samples to enable product quantitation at a small scale. In this method, pellets from 900 μL samples were resuspended in 100 μL of 75 mM NaF. To this suspension 1 mL of 1:1 methanol/chloroform was added and vortexed. Finally, the aqueous phase was removed and dried in a centrivap where 100 μL was used to resuspend the sample. This 9× concentrated sample was then run on HPLC or HPLC-MS. Alternatively, the addition of 4 volumes of ethanol to concentrated wash cells was sufficient to extract the activated deoxysugars, which was then clarified by centrifugation and dried before resuspending and running analytical analysis.

One HPLC method that can be used for analyzing TDP-deoxysugars utilizes an analytical Dionex CarboPac PA1 (Thermo Scientific) column running a H$_2$O and 500 mM ammonium acetate gradient. This method is commonly used for analyzing TDP-deoxysugars produced in vitro. This method also gives moderate separation among closely related TDP-deoxysugars with a runtime of 60 minutes. HPLC-MS analysis used an analytical YMC-Pack ODS-A column running 10 mM trimethylamine (pH 5.6) and acetonitrile gradient coupled with a single quad mass spectrometer running an electron spry ionization probe in negative mode.

2.2 Demonstrating TKDG Production and Accumulation in Engineered Strains.

Overnight seed cultures of zucM01-zucM41 in LB were used to inoculate (5%) fresh 25 mL LB. Strains were allowed to grow to an OD$_{600}$ of ~0.5 at 37° C. before adding 0.5 mM IPTG and moving the flasks to 25° C. No plasmids are present in these particular strains, but IPTG was added and the temperature reduced to standardize the experiments with future production strains. Samples were taken periodically over 72 hrs and the best time points were taken for calculation of production yields (typically between 24-48 hrs). Production yields were extrapolated from the area under the curve obtained by 1 mM thymidine triphosphate (TTP). It is common practice to quantitate TDP-sugars using the molar extinction coefficient of thymidine, due to the unavailability of commercial standards. See Marumo et al., *Eur J Biochem* 1992, 204, 539; Zhang et al., *Journal of the American Chemical Society* 2007, 129, 14670; Kornfeld & Glaser, *J Biol Chem* 1961, 236, 1791.

The accumulation of TKDG is illustrated in FIG. 3. As expected, TKDG is not noticeably accumulated in *E. coli* AB707 (zucM01). Instead TDP-Fuc4Nac and TDP-L-rhamnose are observed. The removal of wecD and wecE (zucM11) results in the loss of a peak at ~27 minutes, which likely corresponds to TDP-Fuc4NAc (no standards available). In addition, zucM11 accumulated more of TDP-L-rhamnose than in the wild-type strain zucM01. TDP-L-rhamnose was confirmed by running standard. This is expected as the removal of one TDP-deoxysugar pathway would funnel all intermediates into the remaining pathway. In zucM21, the loss of TDP-L-rhamnose is clear, but oddly no accumulation of TKDG is observed. With the inactivation of pgi in zucM31, we see a clear accumulation of TKDG (2.9 mg/L) and to a lesser extent in the pgi and zwf mutant zucM41 (1.4 mg/L). These surprising results led us to hypothesize that RmlA is likely the primary source of glucose-1-phosphate thymidylyltransferase activity in *E. coli* AB707 and the removal of rmlA from zucM21-41 was artificially reducing TKDG yields.

We confirmed the importance of RmlA for the accumulation of TKDG experimentally by overexpressing ST_RmlA from *S. thermophilus* in zucM21. This complementation experiment led to the accumulation of TKDG. Based on these results, new deletion strains were created in which the native rmlA would remain intact (Table 1). The presence of native RmlA (zucM51-zucM71) increased TKDG accumulation 2-3 fold compared to (zucM21-zucM41) with 4.1, 5.0 and 4.5 mg/L, respectively (FIG. 3).

2.3 Demonstrating an Increased Yield of TKDG Yield by Overexpressing TKDG Biosynthetic Genes.

Our best metabolic engineered strain of *E. coli*, zucM61, was reproducibly producing roughly 5 mg/L of TKDG. To this strain we overexpressed individually ST_pgm, ST_rmlA and ST_rmlB (from *S. thermophilus*). We found that ST_pgm and ST_rmlB had no effect on the yield of TKDG; however, ST_rmlA overproduction almost tripled TKDG accumulation to 13.5 mg/L. This strain, zucM51 overexpressing ST_rmlA, was designated zucTKDG.

Thus the best TKDG production came when WRcP was combined with overexpression of ST_RmlA (a homologue of RmlA from *Streptococcus thermophilus*).

Example 3. Demonstrating the Utility of TKDG Over-Producing Strains to Produce TDP-Deoxysugars 3.1 Evaluating Protein Expression of Exogenous Biosynthetic Genes for TDP-Deoxysugars.

The ability of zucTKDG to produce 19 TDP-deoxysugars including TDP-D-fucose, TDP-D-fucofuranose, TDP-D-olivose, TDP-L-rhamnose, TDP-L-noviose, TDP-L-eremosamine, TDP-D-angolosamine, TDP-N,N-didemethyl-D-angolosamine, TDP-L-ristosamine, TDP-L-daunosamine, TDP-L-rhodinose, TDP-D-forosamine, TDP-N,N-didemethyl-D-forosamine, TDP-D-desosamine, TDP-4-amino-D-quinovose, TDP-N,N-didemethyl-D-desosamine, TDP-D-mycaminose, and TDP-N,N-didemethyl-D-mycaminose was evaluated.

A small subset of these TDP-deoxysugars was initially tested. These included TDP-D-fucose, TDP-D-fucofuranose, and TDP-D-olivose. The strategy was to clone a variety of exogenous genes corresponding to different homologues in the pathways (identified in FIG. 5A). Genes were cloned as N-terminal $His_6$-tag proteins and the amount of soluble protein expression was characterized (Table 3). The exogenous genes were screened for soluble expression and those that produced soluble protein were used in appropriate combinations to add to zucTKDG to make a specific TDP-deoxysugar. TDP-D-olivose was not produced because the ChlC5 gene was not expressed well in our host and instead we accumulated the intermediate prior to TDP-D-olivose.

TABLE 3

| | | % Expression as N-term $His_6$-tag | | |
|---|---|---|---|---|
| Enzyme | Protein | Soluble | Inclusion Bodies | Expression |
| For TDP-D-fucose and TDP-D-fucofuranose | | | | |
| 4-KR | Fcf1 | 25 | 75 | + |
| Mutase | Fcf2 | 90 | 10 | +++ |
| For TDP-D-olivose | | | | |
| 2,3-DH | SpnO | — | 100 | +++ |
| | KijB1 | 90 | 10 | +++ |
| | OleV | 40 | 60 | ++ |
| 3-KR | SpnN | — | — | − |
| | KijD10 | 90 | 10 | +++ |
| | OleW | 40 | 60 | ++++ |
| 4-KR | UrdR | — | 100 | +++ |
| | ChlC5 | 10 | 90 | + |
| | | 30 | 70 | ++ |
| | | 10 | 90 | + |
| MtmC | | — | — | − |
| | | — | — | − |
| | | — | 100 | ++ |

Figure 5:
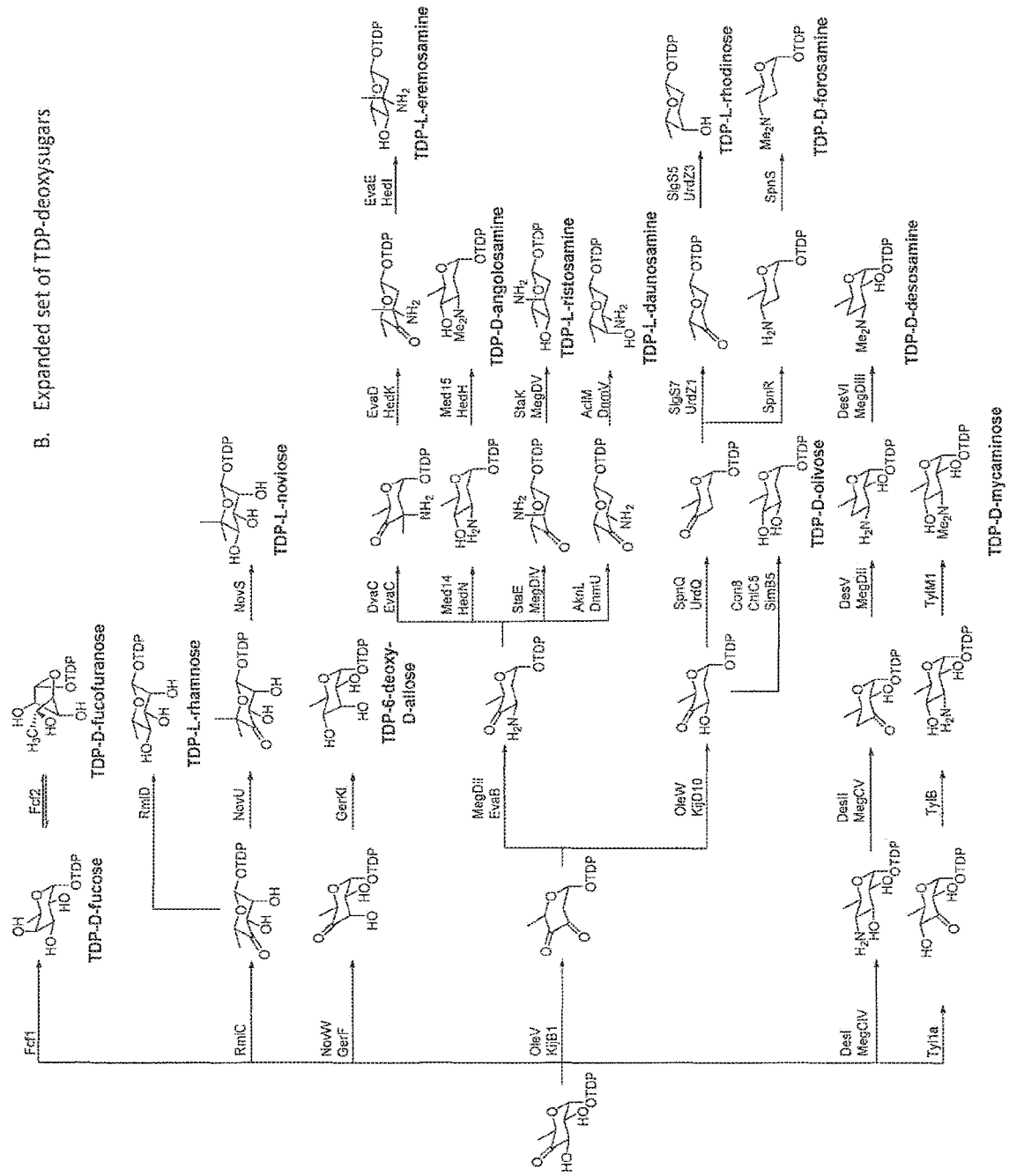
FIG. 5 panels A and B show routes to various TDP-deoxysugars.

Many genes were screened from many different TDP-deoxysugar biosynthetic pathways for soluble expression to expand the number of TDP sugars that could be provided. FIG. 5-B shows some TDP-deoxysugars that were investigated. Some are intermediates in the pathways that can be produced by omitting some genes from the pathway.

The heterologous expression of over fifty proteins (Table 4) in the TKDG production strain, zucTKDG, was tested. These genes represent one or more homologues (indicated by a back slash) for each biosynthetic step of a specific TDP-deoxysugar (Table 5).

TABLE 4

Protein expression of TDP-deoxysugar biosynthetic genes

| Protein | Vector | MCS1 | MCS2 | Expression | Soluble | Insoluble |
|---|---|---|---|---|---|---|
| Fcf1 | pET28a | • | | + | 25% | 75% |
| Fcf2 | pETDuet | • | | +++ | 90% | 10% |
| SpnO | pETDuet | • | | +++ | 0% | 100% |
| OleV | pACYC | • | | +++ | 40% | 60% |
| KijB1 | pACYC | • | | +++ | 90% | 10% |
| OleW | pACYC | | • | +++ | 40% | 60% |
| KijD10 | pACYC | | • | +++ | 90% | 10% |
| SpnN | pETDuet | • | | --- | — | — |
| ChlC5 | pRSF | • | | ++ | 30% | 70% |
| TylMI | pRSF | • | | +++ | 5% | 95% |
| MegDIV | pETDuet | | • | --- | — | — |
| DnmU | pETDuet | | • | +++ | 100% | 0% |
| SpnQ | pETDuet | • | | +++ | 5% | 95% |
| AknL | pETDuet | | • | --- | — | — |
| DvaC | pETDuet | | • | +++ | 50% | 50% |
| SpnR | pETDuet | | • | +++ | 5% | 95% |
| StaE | pETDuet | | • | +++ | 85% | 15% |
| Med14 | pETDuet | | • | --- | — | — |
| EvaB | pETDuet | • | | +++ | 40% | 60% |
| Con8 | pETDuet | • | | --- | — | — |
| SimB5 | pETDuet | • | | --- | — | — |
| UrdZ1 | pETDuet | | • | --- | — | — |
| NovS | pRSF | | • | --- | 5% | 95% |
| Tyl1A | pACYC | • | | ++ | 60% | 40% |
| RmlC | pACYC | • | | +++ | 100% | 0% |
| GerF | pACYC | • | | +++ | 5% | 95% |
| NovW | pACYC | • | | ++ | 100% | 0% |
| EvaE | pACYC | | • | + | 100% | 0% |
| UrdZ3 | pRSF | • | | +++ | 0% | 100% |
| EvaD | pRSF | • | | +++ | 80% | 20% |
| HedK | pRSF | • | | +++ | 10% | 90% |
| DesVI | pRSF | • | | +++ | 10% | 90% |

TABLE 4-continued

Protein expression of TDP-deoxysugar biosynthetic genes

| Protein | Vector | MCS1 | MCS2 | Expression | Soluble | Insoluble |
|---|---|---|---|---|---|---|
| DnmV | pRSF | • | | --- | — | — |
| Med15 | pRSF | • | | +++ | 0% | 100% |
| SpnS | pRSF | • | | +++ | 0% | 100% |
| MegDII | pETDuet | • | | ++ | 60% | 40% |
| StaK | pRSF | • | | ++ | 5% | 95% |
| MegCV | pETDuet | • | | --- | — | — |
| DesV | pETDuet | | • | + | 5% | 95% |
| NovU | pETDuet | • | | ++ | 5% | 95% |
| EvaC | pETDuet | | • | ++ | 5% | 95% |
| SlgS7 | pETDuet | | • | ++ | 75% | 25% |
| HedH | pRSF | • | | ++ | 40% | 60% |
| MegDV | pRSF | • | | --- | — | — |
| AclM | pRSF | • | | ++ | 5% | 95% |
| TylB | pACYC | | • | --- | — | — |
| UrdQ | pETDuet | • | | + | 5% | 95% |
| GerKI | RSF | • | | ++ | 95% | 5% |
| DesII | pETDuet | • | | +++ | 5% | 95% |
| MegCIV | pACYC | • | | ++ | 0% | 100% |
| MegDIII | pRSF | • | | +++ | 60% | 40% |
| DesI | pACYC | • | | + | 10% | 90% |
| HedN | pETDuet | | • | --- | — | — |
| HedI | pRSF | | • | --- | — | — |
| SlgS5 | pRSF | • | | + | 5% | 100% |

TABLE 5

Proteins found in each TDP-deoxysugar biosynthetic pathway

| TDP-deoxysugar produced | | Homologues tested for each biosynthetic step | | | | |
|---|---|---|---|---|---|---|
| TDP-D-fucose (9) | RmIA | Fcf1 | | | | |
| TDP-D-fucofuranose (10) | RmIA | Fcf1 | Fcf2 | | | |
| TDP-D-olivose (11) | RmIA | KijB1/OleV | KijD10/OleW | Con8/SimB5/ChIC5 | | |
| TDP-L-rhamnose (12) | RmIA | RmIC | | | | |
| TDP-L-noviose (13) | RmIA | RmIC | NovU | NovS | | |
| TDP-6-deoxy-D-allose (14) | RmIA | NovW/GerF | GerKI | | | |
| TDP-L-eremosamine (15) | RmIA | KijB1/OleV | B | DvaC/EvaC | EvaD/HedK | EvaE/HedI |
| TDP-D-angolosamine (16) | RmIA | KijB1/OleV | MegDII/EvaB | Med14/HedN | Med15/HedH | |
| TDP-N,N-didemethyl-D-angolosamine (17) | RmIA | KijB1/OleV | MegDII/EvaB | Med14/HedN | | |
| TDP-L-ristosamine (18) | RmIA | KijB1/OleV | MegDII/EvaB | StaE/MegDIV | StaK/MegDV | |
| TDP-L-daunosamine (19) | RmIA | KijB1/OleV | MegDII/EvaB | AknL/DnmU | AclM/DnmV | |
| TDP-L-rhodinose (20) | RmIA | KijB1/OleV | KijD10/OleW | SpnQ/UrdQ | Slg7/UrdZ1 | SlgS5/UrdZ3 |
| TDP-D-forosamine (21) | RmIA | KijB1/OleV | KijD10/OleW | SpnQ/UrdQ | SpnR | SpnS |
| TDP-N,N-didemethyl-D-forosamine (22) | RmIA | KijB1/OleV | KijD10/OleW | SpnQ/UrdQ | SpnR | |
| TDP-D-desosamine (23) | RmIA | DesI/MegCIV | DesII/MegCV | DesV/MegDII | MegDIII/DesVI | |
| TDP-4-amino-D-quinovose (24) | RmIA | DesI/MegCIV | | | | |
| TDP-N,N-didemethyl-D-desosamine (25) | RmIA | DesI/MegCIV | DesII/MegCV | DesV/MegDII | | |
| TDP-D-mycaminose (26) | RmIA | Tyl1a | TylB | TylM1 | | |
| TDP-N,N-didemethyl-D-mycaminose (27) | RmIA | Tyl1a | TylB | | | |

It's important to note that to make L-noviose a different host background, such as WRP (see Table 1), which has all the genes of the rhamnose pathway deleted is needed. If the noviose genes are expressed in WRcP, only L-rhamnose will be produced.

3.2 Constructing Specific TDP-Deoxysugar Production *E. coli* Strains.

Based on the protein expression data, only genes that expressed at least 5% soluble protein (as visualized on SDS-PAGE) in zucTKDG were utilized for production studies. These genes were cloned in the Duet vector system (Novagen) in order to accommodate each possible combination at each step of the biosynthetic pathway for a given TDP-deoxysugar. These plasmid sets were then transformed into zucTKDG and screened for specific TDP-deoxysugar production using HPLC-MS analysis. Strains were tested under several 25 mL shake flask culture conditions. Several variables were manipulated including temperature (25° C. vs 37° C.), IPTG concentration (0.1-1.0 mM), $OD_{600}$ at induction (0.5-5), glucose concentration (0.5%-3%), and media content (1×-4× LB). The optimized conditions were determined to be as follows: overnight seed cultures of each strain in 1×LB were used to inoculate (5%) fresh 25 mL 3×LB+ 0.5% glucose. Strains were allowed to grow to an $OD_{600}$ of ~5.0 at 37° C. before adding 0.5 mM IPTG and moving the flasks to 25° C. Samples were pH adjusted periodically to maintain pH 7.0-8.0. In addition, glucose was monitored by glucose strips (Uriscan) and 0.5% glucose was added when glucose was found to be <0.1%. Production was also found when strains were fed fructose, gluconate and/or glycerol. Samples were taken at several time points and the TDP-deoxysugars were extracted (discussed in 2.1) and analyzed by HPLC-MS. The best production yields of TDP-deoxysugars are summarized in Table 6.

TABLE 6

*E. coli* production of TDP-deoxysugars

| TDP-deoxysugar | Production (mg/L) |
|---|---|
| TDP-D-fucose (9) | 50 |
| TDP-D-fucofuranose (10) | 10 |
| TDP-D-olivose (11) | 14 |
| TDP-L-rhamnose (12) | 27 |
| TDP-L-noviose (13) | 1 |
| TDP-6-deoxy-D-allose (14) | 21 |
| TDP-L-eremosamine (15) | 8 |
| TDP-D-angolosamine (16) | 0 |
| TDP-N,N-didemethyl-D-angolosamine (17) | 0 |
| TDP-L-ristosamine (18) | 0 |
| TDP-L-daunosamine (19) | 0 |
| TDP-L-rhodinose (20) | 0 |
| TDP-D-forosamine (21) | 5 |
| TDP-N,N-didemethyl-D-forosamine (22) | 2 |
| TDP-D-desosamine (23) | 22 |

TABLE 6-continued

E. coli production of TDP-deoxysugars

| TDP-deoxysugar | Production (mg/L) |
|---|---|
| TDP-4-amino-D-quinovose (24) | 19 |
| TDP-N,N-didemethyl-D-desosamine (25) | 32 |
| TDP-D-mycaminose (26) | 0 |
| TDP-N,N-didemethyl-D-mycaminose (27) | 0 |

The production of 12 of the 19 TDP-deoxysugars was successfully realized in the initial attempts. It is highly likely the reason for failure of the remaining TDP-deoxysugars is simply poor protein expression. The production of 16, 17, 26 and 27 (Table 5) was not tested because the lack of soluble expression of proteins responsible for a biosynthetic step in their pathway. The TDP-deoxysugars 18, 19 and 20 (Table 5) had one or more biosynthetic steps where responsible proteins only expressed 5% soluble protein by SDS-PAGE. It is likely that by improving the protein expression of these genes or finding alternative homologues would allow the production of these TDP-deoxysugars in microorganisms such as E. coli.

Example 4. Secretion into Media

Upon optimization of shake flask screening methods the production of TDP-D-fucose in the suite of engineered strains was reinvestigated. Interestingly, significant product in the broth and cell pellet (Table 7) was observed, which was not observed under initial fermentation conditions.

TABLE 7

| Strain | Found in Broth | | Found in Cells | | Combined Totals | |
|---|---|---|---|---|---|---|
| | mg/L | mg/L/OD | mg/L | mg/L/OD | mg/L | mg/L/OD |
| AB707 Fcf1 + RmlA | 56.35 | 6.02 | 32.13 | 3.43 | 88.47 | 9.45 |
| zucM51 Fcf1 + RmlA | 460.21 | 53.33 | 77.15 | 8.94 | 537.36 | 62.27 |
| zucM61 Fcf1 + RmlA | 222.37 | 17.72 | 105.08 | 8.37 | 327.46 | 26.09 |
| zucM91 Fcf1 + RmlA | 50.11 | 5.32 | 52.87 | 5.61 | 102.99 | 10.93 |
| zucM71 Fcf1 + RmlA | 139.14 | 18.70 | 52.22 | 7.02 | 191.36 | 25.72 |
| zucM81 Fcf1 + RmlA | 225.95 | 17.62 | 120.67 | 9.41 | 346.62 | 27.04 |

This indicates that the best strains for intracellular and extracellular accumulation are zucM91 and zucM51, respectively. Overall production was greatest in zucM51 with 85% of TDP-D-fucose found in the fermentation broth. Purification of activated sugars from fermentation broth poses a significant challenge and for some applications intracellular accumulation may be preferred. For these applications zucM81 would be preferred where only 65% of product is accumulated in the media.

Example 5. Integration of Biosynthetic Pathways into Host 5.1 Constructing Integration Plasmids The biosynthetic pathway for overexpression of TKDG and other TDP-deoxysugars was integrated into the chromosome of the microorganism. This allows for additional genes to be easily added via plasmids which could include genes for further modification of sugars or glycosyltransferases for transferring the TDP-deoxysugar to a target moiety. Integration of the GroES/EL heat shock chaperone under an inducible promoter could help facilitate soluble protein folding was also investigated.

The first attempt to integrate genes involved the creation of a plasmid that would allow for the building of operons starting with GroES/EL. PCR was then used to isolate the entire operon and use it in PCR targeted deletion of non-essential metabolic genes in E. coli. The initial plasmid, GROFRTΔ, was designed with GroES/EL downstream of the pTac promoter followed by an MCS and a resistant cassette flanked by FRT sequences for removal of the selection marker after integration (FIG. 6A).

Individual TDP-deoxysugar biosynthetic genes were then placed downstream of groES/EL to make a set of plasmids that would push TDP-deoxysugar synthesis to different branching points beyond TKDG. These were then used as templates for PCR targeted deletion of non-essential metabolic genes in E. coli. This was successful, but when the operons were incorporated into E. coli it was noticed that they would excise back out randomly.

To remedy this unstable integration problem a new approach was tested using the lambda integrase and attP attachment sequence to integrate into the attB site of E. coli. A new plasmid called pIFG was designed (FIG. 6B), which was prepared by inserting the attP attachment sequence in GROFRTΔ. Utilizing this type of plasmid with pLDR8 (E. coli integrating Kit ATCC 77371) we integrated genes into the chromosome of zucM61. The plasmid is first digested with SpeI and re-ligated to remove the replication origin and amp resistance cassette. The resulting plasmid is a suicide vector which is then transformed into the host containing the pLDR8 plasmid providing integrase function. A selection for chloramphenicol resistance results in colonies that are predominantly found to have integrated the suicide vector.

Figure 7:
FIG. 7 panels A, B, C, and D show integration vectors.

To push biosynthesis to individual TDP-deoxysugar pathways pIFGA, pIFGAC, pIFGAKE and pIFGAKK were made (FIG. 7, Table 8). These plasmids should accumulate TKDG, TDP-4-keto-L-rhamnose, TDP-4-keto-2,6-dideoxy-D-glucose and TDP-4-keto-3-amino-2,3,6-trideoxy-D-glucose, respectively. These were then all integrated into the WRcP host to give new strains listed in Table 8. The integration of pIFGAC was also placed in WRP. In WRP, pIFGAC will produce the 4-keto intermediate while in the WRcP host it will produce TDP-L-rhamnose.

TABLE 8

| New strain | Host | Integrated genes |
|---|---|---|
| TD1 | WRcP | groES/EL (pIFG) |
| TD2 | WRcP | groES/EL rmlA (pIFGA) |
| TD3 | WRcP | groES/EL rmlA rmlC (pIFGAC) |
| TD4 | WRcP | groES/EL rmlA kijB1 evaB (pIFGAKE) |
| TD5 | WRcP | groES/EL rmlA kijB1 kijD10 (pIFGAKK) |
| TD6 | WRP | groES/EL rmlA rmlC (pIFGAC) |

Strains TD1-TD6 were also made resistant to an environmental phage that could sometimes infect fermentations by selecting for strains resistant to the page. These strains were named "TD1-TD6 PR", respectively.

5.2. Testing the Chromosome Integrated System

The addition of further exogenous genes to produce TDP-deoxysugar products was tested with these integrated strains. A summary of the various strains produced to make different TDP-deoxysugars is given in Table 9.

added. Incubation is continued at 30° C. overnight. After about 20-24 hrs post-induction, a 900 uL sample is taken for analysis.

Integrated TDP-D-fucose strain: The integrated strain for producing TDP-D-fucose producer had problems. When strain TD2 PR is transformed with 28a-Fcf1 no transformants are obtained. TD2 PR could, however, be transformed

TABLE 9

| TDP-deoxysugar Product | New Strain | Host[1] | pCDFDuet* MCS | pACYC Duet MCS1 | pACYC Duet MCS2 | pET Duet MCS1 | pET Duet MCS2 | pRSF Duet MCS1 | pRSF Duet MCS2 | pET28a MCS |
|---|---|---|---|---|---|---|---|---|---|---|
| D-olivose | DOl1 | TD5 | | | | | | ChlC5 | | |
| D-fucofuranose | DFuf1 | TD2 | | | | | | Fcf2 | Fcf1 | |
| L-Noviose | LNo1 | TD6 | | | | NovU | | NovS | | |
| 6-deoxy-D-allose | 6DA1 | TD2 | | NovW | | | | GerKI | | |
| L-eremosamine | LEr9 | TD4 | | | | | DvaC | EvaD | EvaE | |
| D-forosamine | DFo1 | TD5 | | | | SpnQ | SpnR | SpnS | | |
| desmethyl-D-forosamine | DDFo1 | TD5 | | | | SpnQ | SpnR | | | |
| D-desosamine | DDe2 | TD2 | | DesI | | DesII | DesV | DesVI | | |
| desmethyl-D-desosamine | dDDe1 | TD2 | | DesI | | DesII | DesV | | | |
| D-viosamine | DVi1 | TD2 | | DesI | | | | | | |
| L-ristosamine and/or 4-epi-L-daunosamine | LRi17 | TD4 | | | | | | EvaD | EvaE | |
| D-fucose | DFu1 | TD2 | | | | | | | | Fcf1 |
| L-rhamnose | Lrha | TD3 | | | | | | | | |

[1]Phage resistant versions of these strains used.

The initial production screening gave the following results listed in Table 10 below.

TABLE 10

| Strain | Product | m/z (M − H) | mg/L |
|---|---|---|---|
| DOl1 | D-olivose | 531 | 3.26 ± 0.56 |
| | D-quinovose[2] | 547 | 11.52 ± 1.46 |
| DFuf1 | D-fucose/D-fucofuranose | 547 | 20.87 ± 2.09 |
| LNo1 | L-noviose | 561 | 11.08 ± 0.59 |
| | 5-C-methyl-6-deoxy-L-talose[2] | 561 | 3.7 ± 0.16 |
| | L-rhamnose[2] | 547 | 4.09 ± 0.42 |
| | 6-deoxy-L-talose[2] | 547 | 1.13 ± 0.13 |
| 6DA1 | 6-deoxy-D-allose | 547 | 4.33 ± 0.78 |
| LEr9 | L-eremosamine | 544 | 8.83 ± 0.53 |
| DFo1 | D-forosamine | 542 | 13.59 ± 4.01 |
| | dimethyl-D-pyrrolosamine[2] | 558 | 8.01 ± 1.14 |
| dDFo1 | didesmethyl-D-forosamine | 514 | 0.87 ± 0.42 |
| | D-pyrrolosamine[2] | 530 | 7.71 ± 0.50 |
| DDe2 | didesmethyl-D-desosamine | 530 | 2.57 ± 0.87 |
| | D-viosamine | 546 | 3.22 ± 0.46 |
| | D-desosamine | 558 | 16.36 ± 7.48 |
| dDDe1 | didesmethyl-D-desosamine | 530 | 16.21 ± 4.92 |
| | D-viosamine | 546 | 6.0 ± 2.16 |
| DVi1 | D-viosamine | 546 | 15.92 ± 0.90 |
| LRi17 | L-ristosamine or 4-epi-L-daunosamine | 530 | 8.21 ± 0.30 |
| DFu1 | D-fucose | 547 | 31.09 ± 3.75 |
| LRha | L-rhamnose | 547 | 11.06 ± 2.32 |

[1]Phage resistant versions of strains used in this example.
[2]Expected product.

For small scale screening, 25 mL of modified LB (10 g/L Tryptone, 15 g/L Yeast Extract and 10 g/L NaCl) containing 1× antibiotics or 0.5× antibiotics was used. A 5% seed from an overnight culture tube of the strain is used to inoculate 25 mL of media and 0.5% glucose is added. This is allowed to grow to an $OD_{600}$ of ~2.5-3.0 at 37° C. with shaking. The pH is then adjusted up to ~7.0 if needed, glucose is added (0.5%) if not present, and 0.5 mM IPTG is added. The flask is then placed at 30° C. with shaking and checked every 8 hrs. If needed, pH is again adjusted and glucose (0.5%) is with pRSFDuet-Fcf2/Fcf1. This strain makes TDP-D-fucose primarily with some TDP-D-fucofuranose.

I claim:

1. A method of producing a thymidine diphosphate (TDP)-deoxysugar, comprising:
    culturing a recombinant microorganism comprising Escherichia coli strain zucTKDG in culture medium comprising glucose, fructose, gluconate, glycerol, or combinations thereof, under conditions suitable for conversion of glucose, fructose, gluconate, glycerol, or combinations thereof by the recombinant microorganism to a TDP-deoxysugar; and
    isolating the TDP-deoxysugar,
    wherein the recombinant microorganism:
    (a) comprises a functional deletion of rmlC (dTDP-4-dehydrorhamnose 3,5-epimerase), rmlD (dTDP-4-dehydrorhamnose reductase), wecE (TDP-4-oxo-6-deoxy-D-glucose transaminase), and wecD (TDP-fucosamine acetyltransferase);
    (b) expresses a recombinant rmlA (glucose-1-phosphate thymidylyltransferase); and
    (c) expresses:
        (i) a TDP-deoxysugar biosynthetic protein consisting of Fcf1 to produce TDP-D-fucose;
        (ii) TDP-deoxysugar biosynthetic proteins consisting of Fcf1 and Fcf2 to produce TDP-D-fucofuranose;
        (iii) TDP-deoxysugar biosynthetic proteins consisting of KijB1 or OleV, KijD10 or OleW, and ChlC5 to produce TDP-D-olivose;
        (iv) a TDP-deoxysugar biosynthetic protein consisting of RmlC to produce TDP-L-rhamnose;
        (v) TDP-deoxysugar biosynthetic proteins consisting of RmlC, NovU, and NovS to produce TDP-L-noviose;
        (vi) TDP-deoxysugar biosynthetic proteins consisting of NovW or GerF and GerKI to produce TDP-6-deoxy-D-allose;
        (vii) TDP-deoxysugar biosynthetic proteins consisting of KijB1 or OleV, MegDII or EvaB, DvaC or EvaC, EvaD or HedK, and EvaE to produce TDP-L-eremosamine;

(viii) TDP-deoxysugar biosynthetic proteins consisting of KijB1 or OleV, KijD10 or OleW, SpnQ or UrdQ, and SpnR to produce TDP-N,N-didemethyl-D-forosamine;
(ix) TDP-deoxysugar biosynthetic proteins consisting of DesI, DesII, DesV, or MegDII, and DesVI or MegDIII to produce TDP-D-desosamine;
(x) a TDP-deoxysugar biosynthetic protein consisting of DesI to produce TDP-4-amino-D-quinovose; or (xi) TDP-deoxysugar biosynthetic proteins consisting of DesI or DesII and DesV or MegDII to produce TDP-N,N-didemethyl-D-desosamine.

2. The method of claim 1, wherein one or more aglycones are added to the culture medium.

3. A method of producing a glycosylated TDP-deoxysugar, comprising:
   contacting the isolated TDP-deoxysugar of claim 1 with a glycosyltransferase and an aglycone under suitable reaction conditions to form a reaction mixture; and
   isolating the glycosylated TDP-deoxysugar from the reaction mixture.

4. The method of claim 1, wherein the recombinant rmlA is from *Streptococcus thermophiles*.

5. The method of claim 1, wherein the microorganism further comprises:
   (d) a functional deletion of zwf (glucose-6-phosphate 1-dehydrogenase) and/or ptsG (PTS system glucose-specific transporter).

6. The method of claim 3, wherein the glycosyltransferase comprises one or more of GtfC, EryCIII, AknS, DesVII, SpnG, and MtmGIV.

* * * * *